United States Patent
Perly et al.

(10) Patent No.: US 7,812,152 B2
(45) Date of Patent: Oct. 12, 2010

(54) AMPHIPHILIC CYCLODEXTRIN DERIVATIVES, METHOD FOR PREPARATION THEREOF AND USES THEREOF

(75) Inventors: Bruno Perly, Le Mesnil St Denis (FR); Stéphane Moutard, Marseille (FR); Florence Pilard, Amiens (FR)

(73) Assignee: Commissariat a l'Energie Atomique, Paris (FR)

( * ) Notice: Subject to any disclaimer, the term of this patent is extended or adjusted under 35 U.S.C. 154(b) by 934 days.

(21) Appl. No.: 10/576,346

(22) PCT Filed: Oct. 21, 2004

(86) PCT No.: PCT/FR2004/050519
§ 371 (c)(1), (2), (4) Date: Nov. 20, 2006

(87) PCT Pub. No.: WO2005/042590
PCT Pub. Date: May 12, 2005

(65) Prior Publication Data
US 2007/0142324 A1    Jun. 21, 2007

(30) Foreign Application Priority Data
Oct. 24, 2003    (FR) .................................. 03 50736

(51) Int. Cl.
*A61K 9/127* (2006.01)
*A61K 31/724* (2006.01)
*A61K 8/14* (2006.01)

(52) U.S. Cl. .......................... 536/55; 536/103; 536/124; 424/450; 514/58

(58) Field of Classification Search .................. None
See application file for complete search history.

(56) References Cited

U.S. PATENT DOCUMENTS

| | | | |
|---|---|---|---|
| 5,631,244 | A | 5/1997 | Galons et al. |
| 6,858,723 | B1 | 2/2005 | Auzely-Velty et al. |

FOREIGN PATENT DOCUMENTS

| | | |
|---|---|---|
| EP | 0 624 599 | 11/1994 |
| EP | 0 751 150 | 1/1997 |
| ES | 2 053 399 | 7/1994 |
| FR | 2 681 868 | 4/1993 |
| FR | 2 792 942 | 11/2000 |
| FR | 2 808 691 | 11/2001 |
| WO | WO 00/66635 | 11/2000 |

OTHER PUBLICATIONS

Schaschke, N. et al "Cyclodextrin as carrier of peptide hormones . . . " JACS (1998) vol. 120, pp. 7030-7038.*

Caplus abstract: Nonomura, T. et al "Diastereomeric dipeptide derivatives . . . " Peptide Sci. (2002) vol. 38, pp. 269-272.*

Caplus abstract: Djedaieni-Pilard, F. et al "Potentional formation of intramolecular inclusion complexes . . . " JCS Perkin Trans. 2: Phys. Org. Chem. (1995) vol. 4, pp. 723-730.*

Auzély-Velty, et al. "*Cholesteryl-cyclodextrins: Synthesis and Insertion Into Phospholipid Membranes*";Elsevier Science Ltd. (1999) 82-90.

Moutard,et al. "*Novel Glycolipids Based on Cyclodextrins*"; Journal of Inclusion Phenomena and Macrocyclic Chemistry (2002) 44: 317-322.

* cited by examiner

*Primary Examiner*—Leigh C Maier
(74) *Attorney, Agent, or Firm*—McKenna Long & Aldridge LLP

(57) ABSTRACT

The invention relates to cyclodextrin derivatives of formula (I):

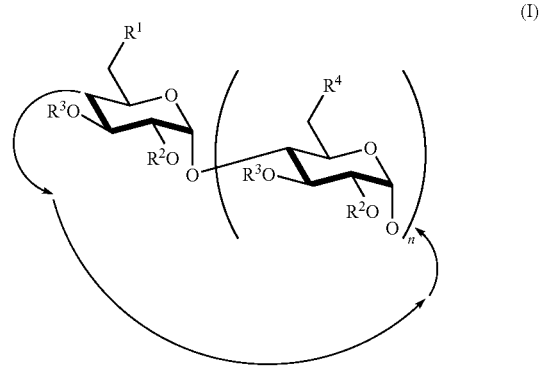

in which:
$R^1 = -NH-E-AA-(L^1)_p(L^2)_q$
where E=a linear or branched $C_1$-$C_{15}$ hydrocarbon-based group with, optionally, one or more hetero atoms; AA=the residue of an amino acid; $L^1$ and $L^2$=a $C_6$-$C_{24}$ hydrocarbon-based group with, optionally, one or more hetero atoms; p and q=0 or 1, at least one being $\neq 0$;
$R^2$=H, —$CH_3$, isopropyl, hydroxypropyl, sulphobutyl ether;
$R^3$=H or $R^2$, except when $R^2$=hydroxypropyl;
all the $R^4$=—OH or $R^2$, except when $R^2$=hydroxypropyl, or at least one of the $R^4$=$R^1$;
n=5, 6 or 7.

The invention also relates to a process for preparing them, and to inclusion complexes and organized surfactant systems comprising them.

27 Claims, No Drawings

AMPHIPHILIC CYCLODEXTRIN DERIVATIVES, METHOD FOR PREPARATION THEREOF AND USES THEREOF

This patent application claims priority to International Application No. PCT/FR2004/050519, filed on Oct. 21, 2004, and French Patent Application No. 0350736, filed on Oct. 24, 2003, which are incorporated herein by reference in their entirety.

DESCRIPTION

1. Technical Field

The present invention relates to novel amphiphilic cyclodextrin derivatives, more specifically α-, β- and γ-cyclodextrin derivatives, and also to the process for the preparation thereof and to the uses thereof.

Besides the fact that they exhibit properties of self-organization in an aqueous medium and of incorporation into organized surfactant systems, these amphiphilic derivatives show notable stability, which makes them particularly easy to manufacture, to conserve and to handle.

They can be used in all the fields of application of cyclodextrins.

However, their ability to incorporate into organized systems can, in particular, be taken advantage of in the pharmaceutical field so as to allow the transport, in particular via the transmembrane pathway, into a living organism, of active ingredients that are poorly water-soluble or water-insoluble, or so as to allow the selective delivery of medicinal products to target organs or cells with a view to optimizing their therapeutic action.

The present invention can also be used in the field of proteomics, for example to transport detergent molecules capable of destroying the lipid layers of cell membranes without however impairing the membrane proteins.

2. Prior Art

Cyclodextrins are non-reducing cyclic oligosaccharides which are obtained industrially by degrading amylose (i.e. the linear form of starch) with cyclodextrin glucosyltransferase, an enzyme of bacterial origin.

The three cyclodextrins most commonly encountered are the α-, β- and γ-cyclodextrins which respectively consist of 6, 7 and 8 D-glucopyranose units, linked to one another via α(1→4) glycoside bonds.

Cyclodextrins have a three-dimensional structure in the shape of a truncated cone, the wall of which is formed by the D-glucopyranose units, in the $^4C_1^{1,2}$ chair conformation and delimits a cavity, also called "cage".

The secondary hydroxyl groups of the D-glucopyranose units are located at the base of the wall of the truncated cone, whereas the primary hydroxyl groups of these units are located at the top of this wall. As a result of this, the outer part of cyclodextrins is naturally hydrophilic, whereas the inner part thereof, which is covered with interglucosidic hydrogen atoms and oxygen atoms, is hydrophobic. This particularity makes it possible to include hydrophobic molecules in the cyclodextrin cage so as to form water-soluble inclusion complexes.

The biodegradable nature of cyclodextrins predisposes them to important applications in the pharmaceutical and agro-foods fields, where the ability of cyclodextrins to serve as a "host" molecule, makes it possible to protect fragile molecules, to ensure the controlled release thereof, or alternatively, in the case of hydrophobic molecules, to ensure the solubilization thereof in an aqueous medium. Pharmaceutical specialty products using cyclodextrins are, moreover, already commercially available.

Over the past fifteen years, many research studies have been carried out with the aim of increasing the amphiphilic nature of cyclodextrins, by grafting one or more hydrophobic groups and thus making them capable of inserting, by virtue of their hydrophobic part, into lipid systems or of self-organizing in an aqueous medium in the form of micelles, without them losing, however, their capacity for complexation with respect to hydrophobic molecules.

In particular, the team of researchers to which the inventors belong has provided, in FR-A-2 792 942 [1], amphiphilic α-, β- or γ-cyclodextrin derivatives obtained by grafting a steroid derivative, via a spacer arm, onto the carbon of the primary hydroxyl group of at least one D-glucopyranose unit of these cyclodextrins. This team was able to obtain, from these derivatives, completely spherical micelles comprising on average 24 monomers and coated at the surface with the cages of these monomers. It was also able to show, by various physicochemical techniques (X-ray scattering, differential calorimetry, $^{31}P$ NMR, etc.), excellent incorporation of these derivatives into phospholipid matrices (Auzély-Velty et al., Carbohydrate Research, 1999, 318, 82-90 [2]).

Now, continuing their studies on cyclodextrins, the inventors have noted that the grafting, still via a spacer arm, of an amino acid carrying one or two lipophilic groups, onto the primary hydroxyl group of at least one D-glucopyranose unit of an α-, β- or γ-cyclodextrin, results in the production of amphiphilic derivatives that are particularly advantageous in so far as they accumulate a very high affinity with respect to organized systems and a notable stability.

It is this observation which forms the basis of the invention.

DISCLOSURE OF THE INVENTION

A subject of the invention is thus amphiphilic cyclodextrin derivatives which correspond to formula (I):

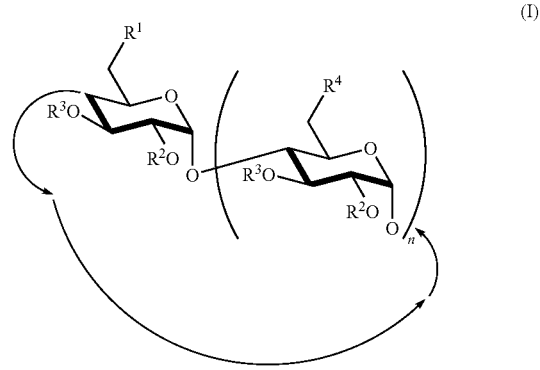

in which:
R¹ corresponds to formula (II):

in which:
E represents a linear or branched, saturated or unsaturated hydrocarbon-based group comprising from 1 to 15 carbon atoms and optionally comprising one or more hetero atoms;
AA represents the residue of an amino acid;

$L^1$ and $L^2$, which may be identical or different, represent a linear, branched and/or cyclic, saturated or unsaturated hydrocarbon-based group comprising from 6 to 24 carbon atoms and optionally comprising one or more hetero atoms;

p and q, which may be identical or different, are integers equal to 0 or to 1, on the condition however that at least one of these integers is other than 0;

$R^2$ represents a hydrogen atom, a methyl group, an isopropyl group, a hydroxypropyl group or a sulphobutyl ether group;

$R^3$ represents a hydrogen atom or is identical to $R^2$, except when $R^2$ is a hydroxypropyl group;

all the $R^4$ represent either a hydroxyl group, or $R^2$, except when $R^2$ is a hydroxypropyl group, or else one or more $R^4$ are identical to $R^1$ and the other $R^4$ represent(s) either a hydroxyl group, or $R^2$, except when $R^2$ is a hydroxypropyl group;

n is an integer equal to 5, 6 or 7.

In the previous and subsequent text, the term "hetero atom" is intended to mean an atom chosen from nitrogen, oxygen, sulphur and the halogens (bromine, iodine, chlorine and fluorine).

Moreover, the expression "residue of an amino acid" is intended to mean the group of atoms which remains of this amino acid when the latter is covalently bonded, firstly, to the spacer arm E and, secondly, to one and/or other of the groups $L^1$ and $L^2$.

According to a first preferred arrangement of the invention, in formula (II), E, which serves as a spacer arm, corresponds to formula (III): —CO—X-$G^1$-, in which X represents a bridge-forming alkylene group comprising from 1 to 8 carbon atoms, while $G^1$ represents a —CO—, —NH— or —NR— group in which R is an alkyl group, advantageously a $C_1$ to $C_6$ alkyl group.

In formula (III), X preferably represents a bridge-forming alkylene group comprising from 1 to 4 carbon atoms, and better still 2 carbon atoms.

The amino acid, the residue of which is symbolized by AA in formula (II), is, preferably, chosen from the twenty amino acids which are conventionally part of the constitution of proteins, namely aspartic acid, glutamic acid, alanine, arginine, asparagine, cysteine, glutamine, glycine, histidine, isoleucine, leucine, lysine, methionine, phenylalanine, proline, serine, threonine, tyrosine, tryptophan and valine.

In particular, it is chosen from aspartic acid, glutamic acid, isoleucine, leucine and phenylalanine, aspartic acid and glutamic acid being particularly preferred.

However, this amino acid can also be chosen from amino acids that are more rare, such as, for example, β-alanine, γ-aminobutyric acid, α-aminoadipic acid, hydroxyproline, hydroxylysine, phenylserine, α,ε-diaminopimelic acid and ornithine, it being possible, a priori for any amino acid to be suitable since it comprises, by definition, two functional groups, one a carboxylic acid, the other an amine, allowing the covalent bonding thereof, firstly, to the spacer arm E, and, secondly, to at least one group $L^1$ or $L^2$.

The choice of the amino acid depends in particular on the value that it is desired to give to p and q in formula (II), in so far as it must comprise at least three functional groups so that p and q can both be equal to 1 (i.e., so that the two groups $L^1$ and $L^2$ are present), whereas it is sufficient—and it is even desirable in order to simplify the preparation of the cyclodextrin derivative—for it to comprise only two functional groups when one of the integers p and q is equal to 0.

In accordance with the invention, it is preferred for AA to be the residue of an amino acid belonging to the L series. However, it is also possible for AA to be the residue of amino acid of the D series.

According to another preferred arrangement of the invention, in formula (II), $L^1$ and/or $L^2$ correspond(s) to formula (IV): -$G^2$-Y in which $G^2$ represents a —CO—, —NH— or —NR— group where R is an alkyl group, advantageously a $C_1$ to $C_6$ alkyl group, while Y represents a $C_8$ to $C_{18}$ linear alkyl chain or a cyclic or polycyclic group known to be lipophilic, such as a steroid group, for example derived from cholesterol, a polyaromatic group, for example derived from naphthalene, from dansyl, or from anthracene or else a group derived from alkaloids.

In formula (IV), Y preferably represents a $C_{12}$ to $C_{16}$ alkyl chain.

Among the cyclodextrin derivatives according to the invention, preference is given to those in which the spacer arm E is bonded via an amide bond to the residue AA, this residue being itself bonded via an amide bond to the group(s) $L^1$ and/or $L^2$, in the interest of ease of preparation.

In this case, E preferably corresponds to the formula: —CO—X—CO— in which X has the same meaning as above, while $L^1$ and/or $L^2$ preferably correspond(s) to the formula: —NH—Y in which Y has the same meaning as above.

In this case also, it is preferred for $R^1$ to correspond to formula (VI):

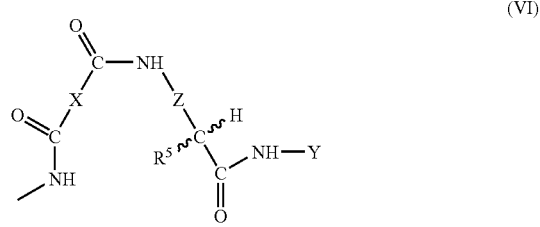

(VI)

in which:

X and Y have the same meaning as above;

while

Z represents:
either a covalent bond, in which case $R^5$ represents a hydrogen atom, a methyl group, the side chain of an amino acid or a group of formula: —$(CH_2)_t$—CO—NH—Y in which t is 1 or 2 and Y has the same meaning as above, or a bridge-forming hydrocarbon-based group, comprising from 1 to 4 carbon atoms and comprising one or more hetero atoms chosen from O and N, in which case $R^5$ represents a primary amine group or a group of formula: —NH—CO—Y in which Y has the same meaning as above.

In particular, when AA represents, in formula (II), the residue of an amino acid chosen from aspartic acid, glutamic acid, isoleucine, leucine and phenylalanine, then, in formula (VI):

Z represents a covalent bond;

Y preferably represents a $C_8$ to $C_{18}$, and better still $C_{12}$ to $C_{16}$, linear alkyl chain;

while $R^5$ represents a branched alkyl group containing 4 carbon atoms, a benzyl group or a group of formula: —$(CH_2)_t$ —CO—NH—Y, in which t is equal to 1 or 2 and Y preferably represents a $C_8$ to $C_{18}$, and better still $C_{12}$ to $C_{16}$, linear alkyl chain.

When AA represents, in formula (II), the residue of an amino acid chosen from aspartic acid and glutamic acid, then, in formula (VI):

Z represents a covalent bond;

Y preferably represents a $C_8$ to $C_{18}$, and better still $C_{12}$ to $C_{16}$, linear alkyl chain;

while $R^5$ represents a group of formula: —$(CH_2)_t$—CO—NH—Y, in which t is equal to 1 or 2 and Y preferably represents a $C_8$ to $C_{18}$, and better still $C_{12}$ to $C_{16}$, linear alkyl chain.

According to yet another preferred arrangement of the invention, the cyclodextrin derivatives comprise only one substituent $R^1$ per molecule of derivative. However, it is equally possible for one or more substituents $R^4$, or even all, to be identical to $R^1$.

The cyclodextrin derivatives according to the invention can be α-, β- or γ-cyclodextrin derivatives. β-cyclodextrin derivatives are preferably used, i.e. the derivatives of formula (I) in which n is equal to 6.

In accordance with the invention, these derivatives can in particular be:

dimethylated, in which case, in formula (I), the $R^2$ are methyl groups, the $R^3$ are hydrogen atoms, while the $R^4$ are methoxy groups when they are not identical to $R^1$, permethylated, in which case, in formula (I), all the $R^2$ and $R^3$ are methyl groups, while the $R^4$ represent methoxy groups when they are not identical to $R^1$, 2-hydroxypropylated, in which case, in formula (I), all the $R^2$ are hydroxypropyl groups, the $R^3$ are hydrogen atoms, while the $R^4$ are hydroxyl groups when they are not identical to $R^1$, sulphobutyl ethers, in which case, in formula (I), the $R^2$, $R^3$ and $R^4$ are hydroxyl groups or sulphobutyl ether groups.

Among the cyclodextrin derivatives according to the invention, preference is most particularly given to:

N',N''-didodecyl-$N_\alpha$-($6^I$-amidosuccinyl-$6^I$-deoxycyclomaltoheptaose)-L-aspartamide, N',N''-didodecyl-$N_\alpha$-($6^I$-amidosuccinyl-$6^I$-deoxycyclomaltoheptaose)-L-glutamide, N',N''-didodecyl-$N_\alpha$-($6^I$-amidosuccinyl-$6^I$-deoxy-$2^I$-O-methylhexakis($2^{II-VII}$,$6^{II-VII}$-di-O-methyl)cyclomaltoheptaose)-L-aspartamide, N',N''-didodecyl-$N_\alpha$-($6^I$-amidosuccinyl-$6^I$-deoxy-$2^I$-O-methylhexakis($2^{II-VII}$,$6^{II-VII}$-di-O-methyl)cyclomaltoheptaose)-L-glutamide, N',N''-didodecyl-$N_\alpha$-($6^I$-amidosuccinyl-$6^I$-deoxy-$2^I$,$3^I$-di-O-methylhexakis($2^{II-VII}$,$3^{II-VII}$,$6^{II-VII}$-tri-O-methyl)cyclomaltoheptaose)-L-aspartamide, N'-dodecyl-N''-hexadecyl-$N_\alpha$-($6^I$-amidosuccinyl-$6^I$-deoxycyclomaltoheptaose)-L-aspartamide, N',N''-didodecyl-$N_\alpha$-($6^I$-amidosuccinyl-$6^I$-deoxy-$2^I$,$3^I$-di-O-methylhexakis($2^{II-VII}$,$3^{II-VII}$,$6^{II-VII}$-tri-O-methyl)cyclomaltoheptaose)-L-glutamide, N',N''-dihexadecyl-$N_\alpha$-($6^I$-amidosuccinyl-$6^I$-deoxy-$2^I$,$3^I$-di-O-methylhexakis($2^{II-VII}$,$3^{II-VII}$,$6^{II-VII}$-tri-O-methyl)cyclomaltoheptaose)-L-aspartamide, and N'-dodecyl-$N_\alpha$-($6^I$-amidosuccinyl-$6^I$-deoxy-$2^I$,$3^I$-di-O-methylhexakis($2^{II-VII}$,$3^{II-VII}$,$6^{II-VII}$-tri-O-methyl)cyclomaltoheptaose)-L-leucinamide.

The cyclodextrin derivatives of formula (I) can be prepared by conventional coupling processes using the corresponding monoamine derivatives of cyclodextrins.

In particular, they can be prepared by a process comprising the coupling of a monoamine derivative of an α-, β- or γ-cyclodextrin grafted beforehand with the spacer arm, with an amino acid grafted beforehand with the group(s) $L^1$ and/or $L^2$.

Thus, a subject of the invention is also a process for preparing cyclodextrin derivatives of formula (I), which comprises a step in which a cyclodextrin derivative of formula (VII):

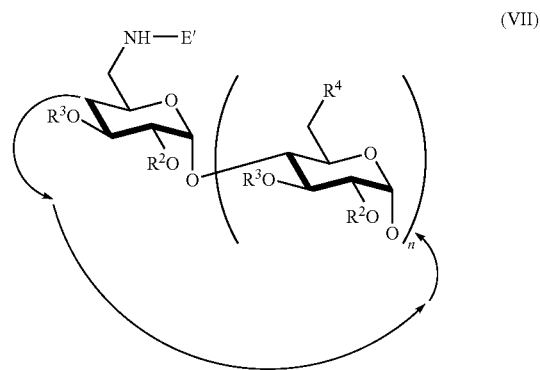

(VII)

in which:

E' represents a linear or branched, saturated or unsaturated hydrocarbon-based group, comprising from 1 to 15 carbon atoms, one or more hetero atoms and a free functional group capable of reacting with a hydroxyl, amine, carboxylic acid or thiol group of an amino acid so as to form a covalent bond;

$R^2$ represents a hydrogen atom, a methyl group, an isopropyl group, a hydroxypropyl group or a sulphobutyl ether group;

$R^3$ represents a hydrogen atom or is identical to $R^2$, except when $R^2$ is a hydroxypropyl group;

all the $R^4$ represent either a hydroxyl group, or $R^2$, except when $R^2$ is a hydroxypropyl group, or else one or more $R^4$ represent an —NH-E' group and the other $R^4$ represent(s) either a hydroxyl group, or $R^2$, except when $R^2$ is a hydroxypropyl group;

n is an integer equal to 5, 6 or 7;

is reacted with a compound of formula (VIII):

in which:

AA' represents an amino acid comprising a free hydroxyl, amine, carboxylic acid or thiol group;

$L^1$ and $L^2$, which may be identical or different, represent a linear, branched and/or cyclic, saturated or unsaturated hydrocarbon-based group comprising from 6 to 24 carbon atoms and, optionally, comprising one or more hetero atoms;

p and q, which may be identical or different, are integers equal to 0 or to 1, on the condition however that at least one of these integers is other than 0.

The free functional group of E' can in particular be a carboxylic acid group, a group derived from a carboxylic acid (acid halide, acid anhydride), a primary or secondary amine group (—NHR where R is an alkyl group, advantageously a $C_1$ to $C_6$ alkyl group), or else a leaving group, depending on the nature of the functional group of the amino acid with which it must react.

In the preceding and subsequent text, the term "leaving group", is intended to mean a group capable of dissociating from the compound which carries it through the attack of a nucleophilic centre. Leaving groups are, for example, halogens, tosylates, mesylates and other sulphonates.

For the preparation of the cyclodextrin derivative of formula (VII), the process according to the invention envisages reacting a monoamine cyclodextrin derivative of formula (IX):

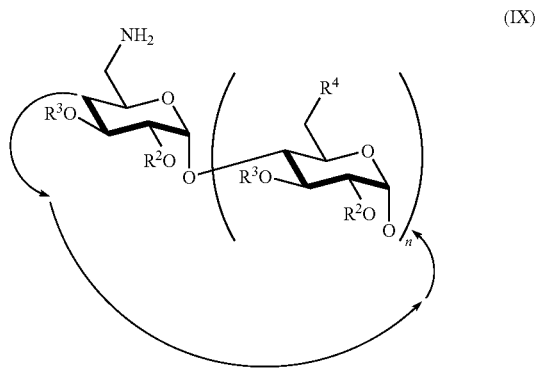

in which:
$R^2$, $R^3$ and n have the same meaning as in formula (VII);
all the $R^4$ represent either a hydroxyl group, or $R^2$, except when $R^2$ is a hydroxypropyl group, or else one or more $R^4$ represent an —$NH_2$ group and the other $R^4$ represent(s) either a hydroxyl group, or $R^2$, except when $R^2$ is a hydroxypropyl group;

with a compound that is a precursor of the group E', which comprises a free functional group capable of reacting with the amine group of the cyclodextrin derivative of formula (IX), this precursor compound becoming the group E' in the course of the reaction.

The compound that is a precursor of the group E' can in particular be a carboxylic acid group, a group derived from a carboxylic acid or a leaving group.

The monoamine cyclodextrin derivative of formula (IX) can, itself, be prepared by subjecting the corresponding monoazide cyclodextrin derivative to a Staudinger reaction, using triphosphine and aqueous ammonia, as described in reference [1].

For the preparation of the compound of formula (VIII), the process according to the invention envisages the following steps:
reacting an amino acid, in which the functional group intended to react with the free functional group of the group E' of the cyclodextrin derivative of formula (VII) has been protected beforehand, with a compound that is a precursor of the group $L^1$ and/or a compound that is a precursor of the group $L^2$, this or these precursor compounds comprising a free functional group capable of reacting with a hydroxyl, amine, carboxylic acid or thiol group of an amino acid so as to form a covalent bond, and becoming the group(s) $L^1$ and/or $L^2$ in the course of the reaction; then
deprotecting the protected functional group of the amino acid.

Of course, when it is desired to graft only one of the two groups $L^1$ and $L^2$ onto the amino acid and when the latter comprises more than two functional groups, then it is advisable to protect all the groups which are not intended to react with the compound that is a precursor of the group $L^1$ or $L^2$ before carrying out this reaction.

Moreover, when it is desired to graft two identical groups $L^1$ and $L^2$ onto the amino acid, this grafting is carried out in a single step by reacting the amino acid with a precursor compound which is the same for the two groups, whereas, when it is desired to graft two different groups $L^1$ and $L^2$ onto the amino acid, this grafting is carried out in two successive steps: a first step in which the amino acid is reacted with one of the compounds that are precursors of the groups $L^1$ and $L^2$, after having protected the functional group of the amino acid intended to react with the other of these compounds, and a second step in which, after deprotection of said functional group, the amino acid is reacted with the other of said precursor compounds.

Here also, the free functional group of the compounds that are precursors of the groups $L^1$ and $L^2$ can in particular be a carboxylic acid group, a group derived from a carboxylic acid, a primary or secondary amine group or a leaving group, depending on the nature of the functional group of the amino acid with which it must react.

When it is desired to prepare one of the preferred cyclodextrin derivatives according to the invention, i.e. a derivative of formula (I) in which R corresponds to formula (VI) above, then:
the compound that is a precursor of the group E' is preferably an acid anhydride of formula (X):

in which X has the same meaning as above, which is reacted with the monoamine cyclodextrin derivative of formula (IX) in an anhydrous medium, for example in anhydrous dimethylformamide, and under an inert atmosphere;
the amino acid, after protection of the amine group intended to react with the carboxylic acid group of the cyclodextrin derivative of formula (XI), for example with an N-(9-fluorenylmethoxycarbonyloxy) (Fmoc) group, is reacted with:
either a single precursor compound of formula: $NH_2$—Y in which Y has the same meaning as above,
or two different precursor compounds of formula: $NH_2$—Y in which Y has the same meaning as above, the reaction then being carried out in two steps with intermediate protection and deprotection operations;
or a precursor compound of formula: $NH_2$—Y and a precursor compound of formula —COOH—Y, in which Y has the same meaning as above, this reaction also being carried out in two steps with intermediate protection and deprotection operations;
the reaction between the cyclodextrin derivative (VII) and the compound of formula (VIII) is preferably carried out in the presence of peptide coupling agents such as N,N'-diisopropylcarbodiimide (DIC) and hydroxybenzotriazol (HOBT) in order to prevent a racemization from occurring.

The amphiphilic cyclodextrin derivatives according to the invention have many advantages, including in particular that of exhibiting both a very high affinity with respect to organized surfactant systems and a notable stability, which means that they can be very readily handled. Thus, these compounds are stable in the solid state, for several months at ambient temperature and exposed to light. They are also stable for several weeks in an aqueous or organic solution, which is not the case with lipid derivatives of phospholipid type, which are stable only at −80° C. They are also relatively simple to prepare, essentially because their synthesis can be carried out by means of conventional peptide coupling processes.

Their affinity with respect to organized surfactant systems and, thus, their ability to incorporate into such systems, can be taken advantage of so as to allow the transport, in particular by the transmembrane pathway, of hydrophobic compounds.

Thus, a subject of the invention is also inclusion complexes of cyclodextrin derivatives of formula (I) with hydrophobic compounds. The latter can be of various types: thus, they may in particular be medicinal active ingredients (steroids, neurotropes, antivirals, bateriostatics, vitamins, etc.) molecules that are useful in cosmetology, contrast products for medical imaging, or else compounds that are useful in proteomics, such as, for example, detergents capable of destroying the lipid layers of cell membranes without affecting the membrane proteins.

small unilamellar vesicles. This is the case, in particular, of dimyristoylphosphatidylcholine which corresponds to the formula above with p=12.

The invention will be understood more clearly on reading the additional description, which refers to examples of preparation of amphiphilic cyclodextrin derivatives according to the invention and which is given by way of nonlimiting illustration.

DETAILED DISCLOSURE OF SPECIFIC EMBODIMENTS

Example 1

N',N''-didodecyl-$N_\alpha$-(6$^I$-amidosuccinyl-6$^I$-deoxycyclomaltoheptaose)-L-aspartamide The title compound, or compound 23, of formula:

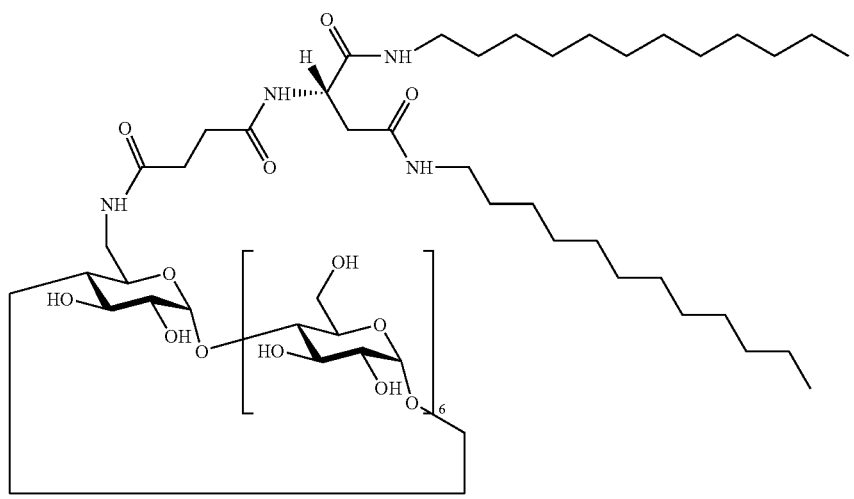

These inclusion complexes can be prepared by conventional processes, for example, by adding, to a solution or a suspension of a cyclodextrin derivative of formula (I), a solution of the hydrophobic compound in a suitable organic solvent, for example acetone.

A subject of the invention is also organized surfactant systems comprising a cyclodextrin derivative of formula (I) or an inclusion complex of this derivative. The surfactants capable of forming such organized systems can be of various types. By way of example, mention may be made of the phospholipids corresponding to the general formula below:

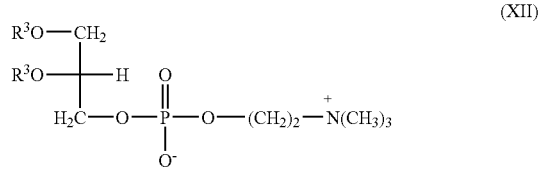

in which $R^3$ represents $CH_3$—$(CH_2)_p$-CO, p being an integer from 6 to 18. These phospholipids are capable of forming is obtained by coupling 6$^I$-amidosuccinyl-6$^I$-deoxycyclomaltoheptaose, or compound 5, with N',N''-didodecyl-L-aspartamide, or compound 21.

1.1. Preparation of Compound 5 a) Preparation of Tosylimidazone, or Compound 1, of Formula

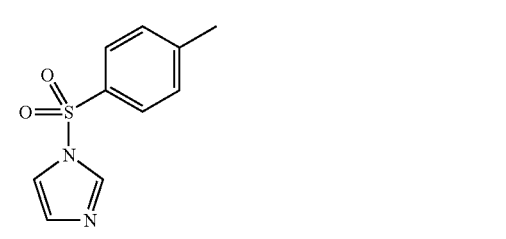

Tosyl chloride (80.27 g; 0.421 mol; 1 eq.) dissolved in 250 ml of dichloromethane is added over 4 hours to imidazole (65.08 g; 0.956 mol; 2.27 eq.) dissolved in 250 ml of dichloromethane, in a 1 litre three-necked flask equipped with a thermometer and under an inert atmosphere. The reaction medium is left stirring overnight at ambient temperature and then filtered over celite and washed with 500 ml of an ethyl acetate/cyclohexane (1/1) mixture. The filtrate is concentrated on a rotary evaporator and the solid residue is then taken up in 50 ml of ethyl acetate and precipitated from 500 ml of cyclohexane. The precipitate formed is filtered off, dried, and taken up in a minimum of dichloromethane. The organic phase is washed with water and then with a saturated sodium chloride solution. The aqueous phase is extracted with dichloromethane. The organic phases are combined, dried over $Na_2SO_4$ and concentrated under reduced pressure. Finally, the residual solid is recrystallized from isopropyl ether. After filtration and washing with ether, compound 1 is obtained with a 75% yield.

TLC: $R_f$=0.6 eluent: $CH_2Cl_2$/MeOH 98/2 (v/v)

M.p.: 78° C.

$^1$H NMR $CDCl_3$ δ (ppm): 8 (s, 1H, $H_3$); 7.82 (d, 2H, $H_{b/b'}$, $^3J_{a-b}$=8 Hz); 7.34 (d, 2H, $H_{c/c'}$, $^3J_{b-a}$=8 Hz); 7.28 (dd, 1H, $^3J$=1.6 Hz, $^3J$=1.4 Hz, $H_2$); 7.08 (m, 1H, $H_3$); 2.42 (s, 3H, $H_e$)

b) Preparation of $6^I$-(O-p-tolylsulphonyl)-$6^I$-deoxy-cyclomaltoheptaose, or compound 2, of formula

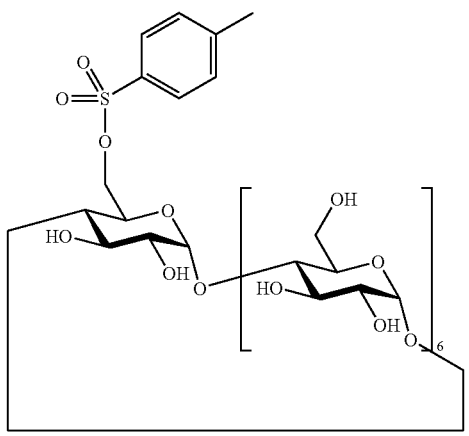

25 g (0.022 mol; 1 eq.) of β-cyclodextrin (Roquette Frères SA) are suspended in 200 ml of distilled water, in a 500 ml Erlenmeyer flask, and then sodium hydroxide chips (8.8 g) are added in a single fraction. The reaction medium becomes clear. Compound 1 (5 g; 0.022 mol; 1 eq.) is rapidly added to the reaction medium (the tosylimidazole remains in suspension). After one hour, the pH is acidified to pH 6 with concentrated HCl. The white precipitate formed is filtered off and then washed with hot distilled water (2×100 ml) and with acetone (3×100 ml), and then recrystallized from water. After filtration and washing with acetone, compound 2 is obtained with a 21% yield.

TLC: $R_f$=0.4 eluent: 6% $NH_4OH$/EtOH/BuOH 5/5/4 (v/v/v)

M.p.: 180° C. (decomposition point between 175° C. and 210° C.)

$^1$H NMR DMSO-d6 δ (ppm): 7.75 (d, 2H, $H_{b/b'}$, $^3J_{a-b}$=9 Hz); 7.4 (d, 2H, $H_{c/c'}$, $^3J_{b-a}$=9 Hz); 5.8-5.5 (m, OH); 4.8 (m, 7H, $H_1$-CD); 4.5-4.3 (m, 2H, $H_6^I$-CD/$H_6^I$-CD); 3.8-3.5 (m, 20H, $H_5$-CD/$H_6^{II-VII}$-CD/$H_{6'}^{II-VII}$-CD/$H_3$-CD); 3.3 (m, 14H, $H_2$-CD/$H_4$-CD); 2.4 (s, 3H, $CH_3$)

ESI-MS+: m/z measured at 1290.2 for $[M+H]^+$, calculated at 1290.2 for $C_{49}H_{77}O_{37}S$ c) Preparation of $6^I$-azido-$6^I$-deoxycyclomaltoheptaose, or compound 3 of formula

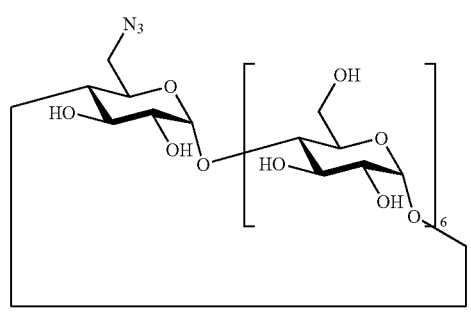

Compound 2 (6.74 g; 0.0052 mol; 1 eq.) is suspended in 550 ml of water, with stirring in a 1 litre round-bottomed flask. An aqueous solution (12.5 ml; 0.052 mol; 10 eq.) of lithium azide at 20% (m/v) (Acros Organics) is added and the reaction medium is refluxed for 4 hours and then left at ambient temperature for 4 days. After filtration of the insoluble material, the solution is concentrated in a rotary evaporator until a volume of 10 ml is obtained. The oily residue is taken up in 190 ml of ethanol and then left in the refrigerator overnight. The mixture obtained is brought to boiling and filtered under hot conditions. The solid is washed with boiling ethanol and then with acetone and dried under vacuum. After lyophilization, compound 3 is obtained with an estimated yield of 60%.

TLC: $R_f$=0.3 eluent: 6% $NH_4OH$/EtOH/BuOH 5/5/4 (v/v/v)

M.p.: 160° C. (decomposition)

$^1$H NMR $D_2O$ δ (ppm): 5.2-5.1 (m, 7H, $H_1$-CD); 4.1-3.8 (m, 30H, $H_3$-CD/$H_5$-CD/$H_6$-CD/$H_{6'}$-CD); 3.75-3.55 (m, 14H, $H_2$-CD/$H_4$-CD)

ESI-MS+: m/z measured at 1166.5 for $[M+Li]^+$, calculated at 1166.4 for $C_{42}H_{69}N_3O_{34}Li$ d) Preparation of $6^I$-amino-$6^I$-deoxycyclomaltoheptaose, or compound 4, of formula

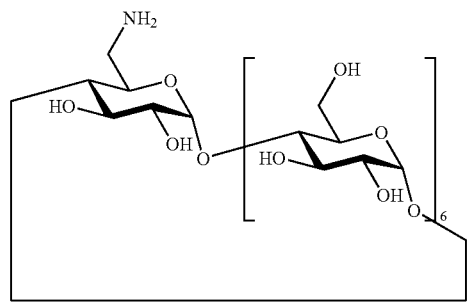

Compound 3 (12.53 g; 0.0108 mol; 1 eq.) is dissolved in 800 ml of DMF, in a 2 litre round-bottomed flask. A solution of triphenylphosphine (11.38 g; 0.043 mol; 4 eq.) dissolved in 40 ml of DMF is added slowly. After 3 hours at ambient temperature with stirring, the reaction medium is cooled to 0° C. and 410 ml of 20% aqueous ammonia are added. The reaction medium is stirred overnight at ambient temperature and is then concentrated in a rotary evaporator. The oily residue is taken up in 600 ml of water, and the white precipitate formed is filtered off and washed with water (2×80 ml). The filtrate is then concentrated under vacuum and the solid residue is taken up in a minimum of water and then brought to pH 4.5 (initial pH of 8.9), the insoluble material is filtered off and the filtrate is passed batchwise over Lewatit® SP 1080 resin (Merck). Compound 4 is detached with 6% aqueous ammonia and the filtrate is then concentrated in a rotary evaporator and taken up in a minimum of water. The insoluble material is filtered off and the filtrate is precipitated from acetone.

After drying under vacuum overnight, 7.25 g of crude product are recovered and again dissolved in water. The insoluble material is filtered off on filter paper and the filtrate is brought to pH 4.5. Half is then passed over a column of Lewatit® SP 1080 resin and the rest batchwise.

The various fractions are evaporated to dryness and then taken up in a minimum of water and, finally, lyophilized. Compound 4 is obtained with an overall yield over the 2 steps of 45%.

TLC: $R_f$=0.2 eluent: 6% $NH_4OH/EtOH/BuOH$: 5/5/4 (v/v/v)

M.p.: 160° C. (decomposition)

$^1$H NMR $D_2O$ δ (ppm): 5.2-5.05 (m, 7H, $H_1$-CD); 4.1-3.75 (m, 28H, $H_3$-CD/$H_5$-CD/$H_6^{II-VII}{}_{CD}$/$H_6^{II-VII}$-CD); 3.75-3.5 (m, 14H, $H_2$-CD/$H_4$-CD); 3.25 (d, 1H, $H_6^I$-CD, $^3J_{6-5}$=10 Hz); 3.05 (d, 1H, $H_6^I$-CD, $^3J_{6-5}$=10 Hz)

ESI-MS+: m/z measured at 1134.5 [M+H]$^+$, calculated at 1134.4 for $C_{42}H_{72}NO_{34}$ e) Preparation of 6$^I$-amidosuccinyl-6$^I$-deoxycyclomaltoheptaose, or compound 5, of formula

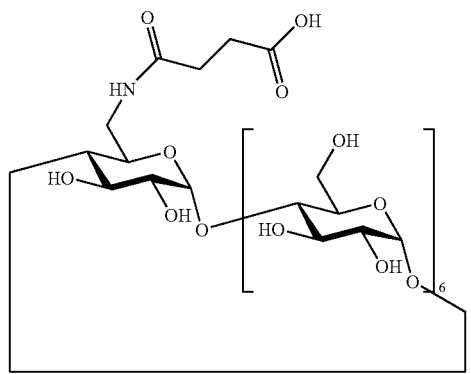

5

Compound 4 (1 g; 0.88 mmol; 1 eq.) is dissolved in 20 ml of anhydrous DMF under an inert atmosphere, in a clean and dry 100 ml round-bottomed flask. Succinic anhydride (0.135 g; 1.34 mmol; 1.5 eq.) dissolved in 6 ml of anhydrous DMF is added. The reaction medium is left under an inert atmosphere for 18 hours at ambient temperature. The reaction is stopped with 120 µL of water and the solution is then precipitated from 200 ml of acetone. The solid obtained is filtered off and then dried in a desiccator. The solid is taken up in a minimum of water, the insoluble material is filtered off and the filtrate is lyophilized. Compound 5 is obtained with a 55% yield.

TLC: $R_f$=0.6 eluent: DMF/BuOH/$H_2O$ 1/2/1 (v/v/v)

M.p.: 160° C. (decomposition)

$^1$H NMR pyridine-d5 δ (ppm): 8.75 (s, 1H, NH-CD); 7.9-7.6 (14OH); 5.8-5.55 (m, 7H, $H_1$-CD); 4.95-3.95 (m, $H_3$-CD/$H_6$-CD/$H_6$'-CD/$H_5$-CD/$H_4$-CD/$H_2$-CD); 3 (m, 4H, $H_b$/$H_c$)

ESI-MS+: m/z measured at 1234.5 [M+H]$^+$, calculated at 1234.4 for $C_{46}H_{76}NO_{37}$ 1.2. Preparation of Compound 21 a) Preparation of $N_α$-(9-fluorenylmethoxycarbonyl)-L-aspartic acid, or compound 17, of formula

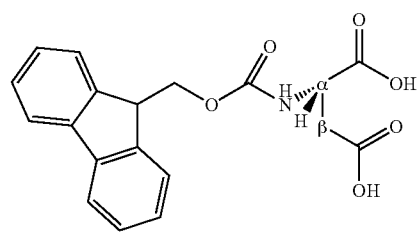

17

3.03 g (22.8 mmol; 1.2 eq.) of L-aspartic acid (Fluka) are dissolved in 54 ml (68.8 mmol; 3.6 eq.) of a 13.5% (m/v) aqueous sodium carbonate solution, in a dry 250 ml round-bottomed flask. The medium is cooled in an ice bath at 0° C., then a solution of 6.41 g (19.0 mmol; 1 eq.) of N-(9-fluorenylmethoxycarbonyloxy)succinimide (N-Fmoc) dissolved in 44 ml of DMF is added with vigorous stirring (a precipitate forms in the reaction medium).

The stirring is maintained for 1 hour at ambient temperature. The mixture is then diluted in 665 ml of water, and extracted with ether (1×80 ml) then with ethyl acetate (2×60 ml). The resulting aqueous phase is cooled in an ice bath and acidified to pH 2 with concentrated (6 N) hydrochloric acid. The aqueous phase containing the precipitated product (in the form of an oil) is extracted with ethyl acetate (6×60 ml). The organic phase derived from the extraction is washed with a saturated aqueous sodium chloride solution (3×35 ml), and then with water (2×35 ml), dried over sodium sulphate, and concentrated in a rotary evaporator (35° C.) until a small residual volume is obtained.

Compound 17 is recrystallized by adding petroleum ether (approximately 10 times the residual volume) with vigorous stirring. After having allowed the mixture to separate by settling out for 2 hours at 4° C., the precipitate is filtered off and then dried for 24 hours in a vacuum oven. 6.22 g (17.5 mmol) of compound 17 are isolated in the form of a fine white powder.

Empirical formula: $C_{19}H_{17}NO_6$, M=355.35 g·mol$^{-1}$

Yield: 92%

M.p.: 181° C.

TLC: $R_f$=0.8 eluent: 60% AcOH/BuOH 4/6 (v/v)

ESI-MS+: m/z measured at 378.1 [M+Na]$^+$, calculated at 378.1 for $C_{19}H_{17}NO_6Na$ $^1$H NMR (dmso-d$_6$, 500.13 MHz) δ (ppm): 12.60 (broad s, 2H, COOH); 7.89 (d, 2H, H-4/H-4', $^3J_{4-3}$=$^3J_{4'-3'}$=7.5 Hz); 7.72 (d, 1H, $N_α$H); 7.70 (d, 2H, H-1/H-1', $^3J_{1-2}$=$^3J_{1'-2'}$=7.5 Hz); 7.42 (t, 2H, H-3/H-3', $^3J_{3-2}$=$^3J_{3-4}$=$^3J_{3'-2'}$=$^3J_{3'-4'}$=7.5 Hz); 7.33 (t, 2H, H-2/H-2', $^3J_{2-1}$=$^3J_{2-3}$=$^3J_{2'-1'}$=$^3J_{2'-3'}$=7.5 Hz); 4.34 (m, 1H, H-α); 4.29 (d, 2H, H-8); 4.22 (t, 1H, H-7); 2.73 (dd, 1H, H-β, $^3J_{β-α}$=5.5 Hz, $^3J_{β-β'}$=16.4 Hz); 2.58 (dd, 1H, H-β', $^3J_{β'-α}$=8.3 Hz, $^3J_{β-β'}$=16.4 Hz)

$^{13}$C NMR (dmso-d$_6$, 125.77 MHz) δ (ppm): 172.8, 171.8 ($C_αH$—COOH, $C_βH_2$—COOH); 155.9 (C-9); 143.9 (C-5/C-5'); 140.8 (C-6/C-6'); 127.7 (C-3/C-3'); 127.2 (C-2/C-2'); 125.4 (C-1/C-1'); 120.2 (C-4/C-4'); 65.8 (C-8); 50.6 (C-α); 46.7 (C-7); 36.1 (C-β)

b) Preparation of N',N''-didodecyl-$N_\alpha$-(9-fluorenyl-methoxycarbonyl)-L-aspartamide, or compound 19, of formula

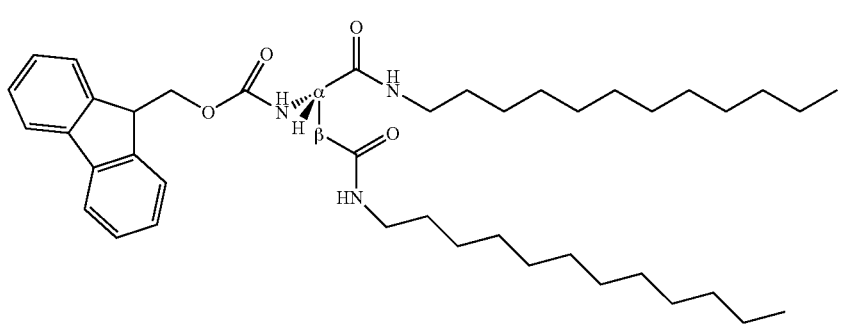

19

5.03 g (14.2 mmol; 1 eq.) of compound 17 are dissolved in 30 ml of anhydrous DMF with stirring and under an inert atmosphere, in a dry 500 ml round-bottomed flask. 6.6 ml (42.5 mmol; 3 eq.) of N,N'-diisopropyl-carbodiimide (DIC) then 5.74 g (42.5 mmol; 3 eq.) of hydroxybenzotriazole (HOBT), in solution in 20 ml of anhydrous DMF, are successively added.

The reaction is maintained at ambient temperature over 2 hours with stirring and under an inert atmosphere. 7.91 g (42.7 mmol; 3 eq.) of dodecylamine, in solution in 100 ml of anhydrous chloroform (freshly distilled over $P_2O_5$), are, finally, added to the reaction medium and the entire mixture is left at ambient temperature for 24 hours, with stirring and under an inert atmosphere (an abundant precipitate rapidly forms). The mixture is then concentrated in a rotary evaporator (40° C.) and taken up in DMF. The pasty solid is filtered off and washed, firstly with DMF, then with ether. After drying overnight in a vacuum oven, 6.95 g (10.1 mmol) of compound 19 are isolated in the form of a fine white powder.

Empirical formula: $C_{43}H_{67}N_3O_4$, M=690.02 g·mol$^{-1}$

Yield: 71%

M.p.: 174° C.

TLC: $R_f$=0.9 eluent: $CHCl_3$/MeOH 9/1 (v/v)

$^1$H NMR (CDCl$_3$, 500.13 MHz) δ (ppm): 7.78 (d, 2H, H-4/H-4', $^3J_{4-3}$=$^3J_{4'-3'}$=7.5 Hz); 7.61 (d, 2H, H-1/H-1', $^3J_{1-2}$=$^3J_{1'-2'}$=7.5 Hz); 7.41 (tt, 2H, H-3/H-3', $^3J_{3-2}$=$^3J_{3-4}$=$^3J_{3'-2'}$=$^3J_{3'-4'}$=7.5 Hz); 7.32 (tt, 2H, H-2/H-2', $^3J_{2-1}$=$^3J_{2-3}$=$^3J_{2'-1'}$=$^3J_{2'-3'}$=7.5 Hz); 7.00 (broad t, 1H, N'H); 6.55 (d, 1H, $N_\alpha$H); 5.85 (broad t, 1H, N''H); 4.48 (broad m, 1H, H-α); 4.42 (d, 2H, H-8, $^3J_{8-7}$=7.2 Hz); 4.23 (t, 1H, H-7, $^3J_{7-8}$=7.2 Hz); 3.23 (m, 4H, H-1α/H-1β); 2.87 (d, 1H, H-β, $^3J_{\beta-\beta'}$=14.8 Hz); 2.52 (dd, 1H, H-β', $^3J_{\beta'-\alpha}$=6.8 Hz, $^3J_{\beta-\beta'}$=14.8 Hz); 1.49 (m, 4H, H-2α/H-2β); 1.25-1.32 (m, H-3α to H-11α/H-3β to H-11β); 0.89 (t, 6H, H-12α/H-12β)

$^{13}$C NMR (CDCl$_3$, 125.77 MHz) δ (ppm): 170.9, 170.3 (—CO—N'H, —CO—N''H); 156.1 (C-9); 143.6 (C-5/C-5'); 141.2 (C-6/C-6'); 127.6 (C-3/C-3'); 127.0 (C-2/C-2'); 125.0 (C-1/C-1'); 119.9 (C-4/C-4'); 67.1 (C-8); 51.6 (C-α); 47.0 (C-7); 39.6 (C-1α/C-1β); 37.9 (C-β); 31.8 (C-10α/C-10β); 29.1-29.6 (C-2α, C-4α to C-9α/C-2β, C-4β to C-9β); 26.8 (C-3α/C-3β); 22.6 (C-11α/C-11β); 14.0 (C-12α/C-12β)

c) Preparation of N',N''-dodecyl-L-aspartamide, or compound 21, of formula

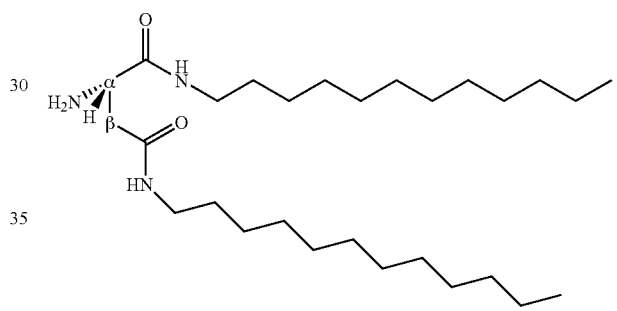

21

2.09 g (3.03 mmol; 1 eq.) of compound 19 are dissolved in 40 ml of a 20% (v/v) solution of piperidine in chloroform in a 100 ml round-bottomed flask. The solution is heated for a few minutes at 40° C. The reaction medium, which is first heterogeneous due to the poor solubility of the starting product in chloroform, rapidly becomes clear. The solution is then evaporated to dryness, under a primary vacuum (40° C.), so as to remove the maximum amount of piperidine (bp 101-106° C.). The solid residue is taken up in 10 ml of chloroform so as to then be precipitated from 200 ml of hexane, with stirring. After having allowed the mixture to separate by settling out for 2 hours at 4° C., the precipitate is filtered off and then dried. A final step consisting of recrystallization from methanol (dissolution in a minimum of boiling methanol, filtration of the insoluble material under hot conditions and recrystallization at 4° C.) makes it possible to isolate, by filtration, and after drying overnight in a vacuum oven, 1.20 g (257 mmol) of compound 21 in the form of a white powder.

Empirical formula: $C_{28}H_{57}N_3O_2$, M=467.78 g·mol$^{-1}$

Yield: 85%

M.p.: 121° C.

TLC: $R_f$=0.4 eluent: $CHCl_3$/MeOH 9/1 (v/v)

$[\alpha]_D^{20}$+5° (c 0.27, CHCl$_3$)

IR: 3311 cm$^{-1}$ (broad) ν(NH$_2$); 1630 cm$^{-1}$ ν(C=O amides)

ESI-MS+: m/z measured at 468.5 [M+H]$^+$, calculated at 468.5 for $C_{28}H_{58}N_3O_2$; m/z measured at 490.5 [M+Na]$^+$, calculated at 490.4 for $C_{28}H_{57}N_3O_2Na$.

$^1$H NMR (CDCl$_3$, 500.13 MHz) δ (ppm): 7.51 (t, 1H, N'H, $^3J_{N'H-1\alpha}$=5.7 Hz); 6.26 (t, 1H, N"H, $^3J_{N"H-1\beta}$=5.5 Hz); 3.65 (dd, 1H, H-α, $^3J_{\alpha-\beta}$=4.5 Hz, $^3J_{\alpha-\beta'}$=7.1 Hz); 3.21 (m, 4H, H-1α/H-1β); 2.61 (dd, 1H, H-β, $^3J_{\beta-\alpha}$=4.5 Hz, $^3J_{\beta-\beta'}$=14.4 Hz); 2.54 (dd, 1H, H-β', $^3J_{\beta'-\alpha}$=7.1 Hz, $^3J_{\beta'-\beta}$=14.4 Hz); 1.48 (m, 4H, H-2α/H-2β); 1.25-1.32 (m, H-3α to H-11α/H-3β to H-11β); 0.88 (t, 6H, H-12α/H-12β)

$^{13}$C NMR (CDCl$_3$, 125.77 MHz) δ (ppm): 173.7 (—CO—N'H); 170.8 (—CO—N"H); 52.7 (C-α); 40.9 (C-β); 39.4, 39.2 (C-1α, C-1β); 31.8 (C-10α/C-10β); 29.1-29.6 (C-2α, C-4α to C-9α/C-2β, C-4β to C-9β); 26.8 (C-3α/C-3β); 22.6 (C-11α/C-11β); 14.0 (C-12α/C-12β)

1.3. Preparation of Compound 23

407.7 mg (0.33 mmol; 1 eq.) of compound 5, lyophilized beforehand, are dissolved in 10 ml of anhydrous DMF with stirring and under an inert atmosphere in a dry 100 ml round-bottomed flask. 205 μl (1.32 mmol; 4 eq.) of DIC and then 179.3 mg (1.33 mmol; 4 eq.) of HOBT, in solution in 5 ml of anhydrous DMF, are successively added. The reaction is maintained at ambient temperature for 2 hours with stirring and under an inert atmosphere.

185.3 mg (0.40 mmol; 1.2 eq.) of compound 21, dissolved in 15 ml of anhydrous chloroform (freshly distilled over P$_2$O$_5$), are added to the reaction medium. After stirring at ambient temperature and under an inert atmosphere for 24 hours, the reaction is stopped by adding 100 μl of water. The solution is concentrated in a rotary evaporator (40° C.) until an oily residue is obtained, which is then precipitated from 100 ml of acetone with stirring. The precipitate is recovered by centrifugation (10 000 rpm; 15 min), washed with clean acetone and dried overnight under a hood. 486.8 mg of crude product are thus isolated and are purified by normal phase polarity HPLC (μPorasil®; A/B 20/80 (v/v) with A: CH$_3$OH and B: CHCl$_3$/CH$_3$OH/NH$_3$ 20% (80/19.5/0.5) (v/v/v) in 20 min). 465.9 mg (0.28 mmol) of compound 23 are isolated in the form of a fine white powder after lyophilization.

Empirical formula: $C_{74}H_{130}N_4O_{38}$, M=1683.85 g·mol$^{-1}$
Yield: 85%
M.p.: 160° C. (decomp.)
TLC: $R_f$=0.2 eluent: CHCl$_3$/MeOH/H$_2$O 6/3/0.5 (v/v/v)
$[α]_D^{20}$+83° (c 0.26, DMF)
ESI-HRMS (high resolution with detection in the positive mode): m/z measured at 1683.8441 [M+H]$^+$, calculated at 1683.8441 for $C_{74}H_{131}N_4O_{38}$ (deviation: 0 ppm); m/z measured at 1705.8169 [M+Na]$^+$, calculated at 1705.8261 for $C_{74}H_{130}N_4O_{38}Na$ (deviation: 5.4 ppm)

$^1$H NMR (pyridine-d$_5$, 500.13 MHz) δ (ppm): 9.14 (d, 1H, N$_\alpha$H); 8.80 (t, 1H, NH$_{CD}$); 8.68 (t, 1H, N"H); 8.51 (t, 1H, N'H); 5.38 (m, 1H, H-α); 5.42-5.61 (m, 6H, H-1$^{II-VII}{}_{CD}$); 5.43 (d, 1H, H-1$^I{}_{CD}$); 4.62-4.75 (m, H-3$^{II-VII}{}_{CD}$); 4.62 (H-3$^I{}_{CD}$); 4.55-4.64 (m, H-6$^{II-VII}{}_{CD}$); 4.31-4.52 (m, H-5$^{II-VII}{}_{CD}$/H-6$^{II-VII}{}_{CD}$); 4.42 (H-5$^I{}_{CD}$); 4.15-4.29 (m, H-4$^{II-VII}{}_{CD}$); 4.19 (H-6$^I{}_{CD}$); 4.06 (H-6'$^I{}_{CD}$); 3.99-4.14 (m, H-2$^{II-VII}{}_{CD}$); 3.91 (dd, 1H, H-2$^I{}_{CD}$); 3.81 (t, 1H, H-4$^I{}_{CD}$); 3.36, 3.31 (2m, 4H, H-1α, H-1β); 3.12 (d, 1H, H-β); 3.07 (d, 1H, H-β'); 2.5-3.0 (m, 4H, H-b/H-c); 1.53, 1.46 (2m, 4H, H-2α, H-2β); 1.20, 1.18 (H-3α, H-3β); 1.13 (H-11α/H-11β); 1.05-1.25 (m, H-4α to H-10α/H-4β to H-10β); 0.75 (t, 6H, H-12α/H-12β)

$^{13}$C NMR (pyridine-d$_5$, 125.77 MHz) δ (ppm): 173.6 (C-a); 173.4 (C-d); 172.3 (—CO—N'H); 171.5 (—CO—N"H—); 104.1-104.6 (C-1$^{I-VII}{}_{CD}$); 85.8 (C-4$^I{}_{CD}$); 83.7-84.3 (C-4$^{II-VII}{}_{CD}$); 74.1-75.4 (C-3$^{I-VII}{}_{CD}$/C-5$^{II-VII}{}_{CD}$/C-2$^{I-VII}{}_{CD}$); 72.3 (C-5$^{I-VII}{}_{CD}$); 62.6 (C-6$^I{}_{CD}$); 61.9-62.3 (C-6$^{I-VII}{}_{CD}$); 52.0 (C-α); 40.3, 40.5 (C-1α, C-1β); 39.1 (C-β); 32.6 (C-10α/C-10β); 32.1, 32.4 (C-b, C-c); 30.5 (C-2α/C-2β); 30.1 (C-4α/C-4β); 30.1-30.6 (C-5α to C-9α/C-5β to C-9β); 27.8, 27.9 (C-3α, C-3β); 23.4 (C-11α/C-11β); 14.8 (C-12α/C-12β)

Example 2

Preparation of N',N"-didodecyl-N$_\alpha$-(6$^I$-amidosuccinyl-6$^I$-deoxycyclomaltoheptaose)-L-glutamide The title compound, or compound 24, of formula:

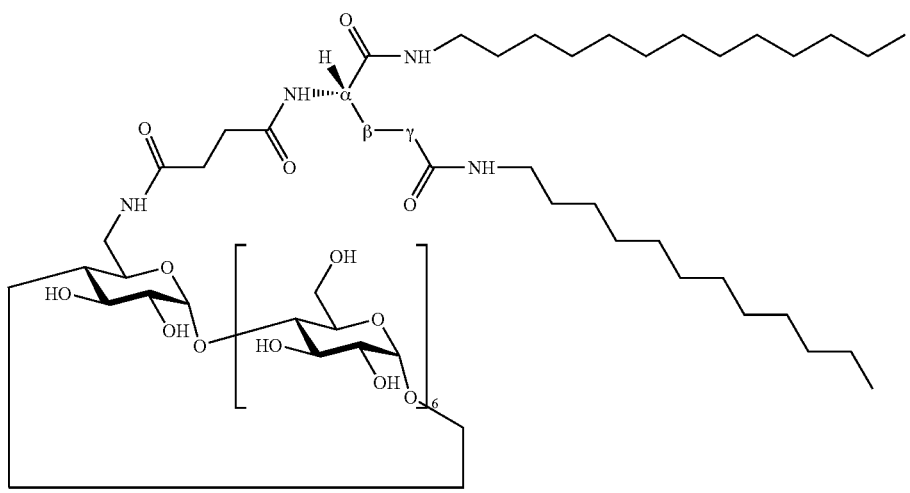

is obtained by coupling compound 5 synthesized in example 1 above, with N',N"-didodecyl-L-glutamide, or compound 22.

2.1. Preparation of Compound 22 a) Preparation of $N_\alpha$-(9-fluorenylmethoxycarbonyl)-L-glutamic Acid, or compound 18, of formula

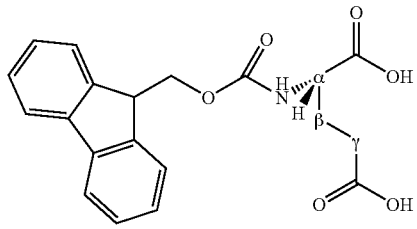

Compound 18 is prepared by following the same experimental protocol as that described for the preparation of compound 17 in example 1 above, but using:
- 3.40 g (23.1 mmol; 1.2 eq.) of L-glutamic acid (Fluka)
- 54.5 ml (69.3 mmol; 3.6 eq.) of 13.5% (m/v) aqueous sodium carbonate solution, and
- 6.50 g (19.3 mmol; 1 eq.) of N-(fluorenylmethoxycarbonyloxy)succinimide.

6.07 g (16.4 mmol) of compound 18 are thus obtained.
Empirical formula: $C_{20}H_{19}NO_6$, M=369.37 g·mol$^{-1}$
Yield: 85%
M.p.: 197° C.
TLC: $R_f$=0.9 eluent: 60% AcOH/BuOH 4/6 (v/v)
ESI-MS+: m/z measured at 392.2 [M+Na]$^+$, calculated at 392.1 for $C_{20}H_{19}NO_6Na$; m/z measured at 408.2 [M+K]$^+$, calculated at 408.1 for $C_{20}H_{19}NO_6K$
$^1$H NMR (dmso-d$_6$, 500.13 MHz) δ (ppm) 12.42 (broad s, 2H, COOH); 7.89 (d, 2H, H-4/H-4', $^3J_{4-3}$=$^3J_{4'-3'}$=7.5 Hz); 7.72 (d, 2H, H-1/H-1', $^3J_{1-2}$=$^3J_{1'-2'}$=7.5 Hz); 7.67 (d, 1H, N$_\alpha$H, $^3J_{N\alpha H-H\alpha}$=8.2 Hz); 7.42 (t, 2H, H-3/H-3', $^3J_{3-2}$=$^3J_{3-4}$=$^3J_{3'-2'}$=$^3J_{3'-4'}$=7.5 Hz); 7.33 (t, 2H, H-2/H-2', $^3J_{2-1}$=$^3J_{2-3}$=$^3J_{2'-1'}$=$^3J_{2'-3'}$=7.5 Hz); 4.28 (d, 2H, H-8); 4.23 (t, 1H, H-7); 4.00 (ddd, 1H, H-α, $^3J_{\alpha-\beta}$=5.0 Hz, $^3J_{\alpha-\beta'}$=1.6 Hz, $^3J_{\alpha-N\alpha H}$=8.2 Hz); 2.32 (m, 1H, Hγ); 1.99 (m, 1H, H-β); 1.79 (m, 1H, H-β')

b) Preparation of N',N"-didodecyl-$N_\alpha$-(9-fluorenylmethoxycarbonyl)-L-glutamide, or compound 20, of formula

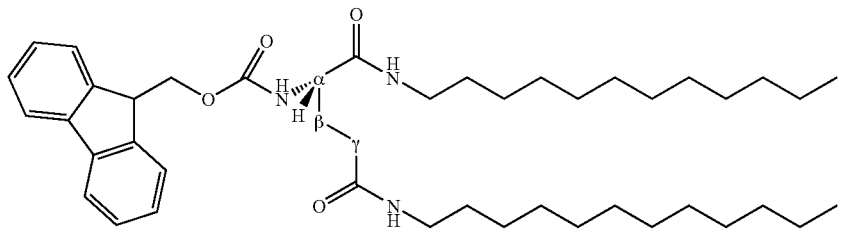

Compound 20 is prepared by following the same experimental protocol as that described for the preparation of compound 19, in example 1 above, but using:
- 5.89 g (16.0 mmol; 1 eq.) of compound 18
- 7.4 ml (47.8 mmol; 3 eq.) of DIC
- 6.47 g (47.9 mmol; 3 eq.) of HOBT
- 8.87 g (47.9 mmol; 3 eq.) of dodecylamine.

9.29 g (13.2 mmol) of compound 20 are thus obtained.
Empirical formula: $C_{44}H_{69}N_3O_4$, M=704.05 g·mol$^{-1}$
Yield: 83%
M.p.: 165° C.
TLC: $R_f$=0.9 eluent: CHCl$_3$/MeOH 9/1 (v/v)
$^1$H NMR (CDCl$_3$, 500.13 MHz) δ (ppm): 7.77 (d, 2H, H-4/H-4', $^3J_{4-3}$=$^3J_{4'-3'}$=7.5 Hz); 7.61 (d, 2H, H-1/H-1', $^3J_{1-2}$=$^3J_{1'-2'}$=7.5 Hz); 7.41 (t, 2H, H-3/H-3', $^3J_{3-2}$=$^3J_{3-4}$=$^3J_{3'-2'}$=$^3J_{3'-4'}$=7.5 Hz); 7.32 (t, 2H, H-2/H-2', $^3J_{2-1}$=$^3J_{2-3}$=$^3J_{2'-1'}$=$^3J_{2'-3'}$=7.5 Hz); 6.69 (broad t, 1H, N'H); 6.24 (broad d, 1H, N$_\alpha$H, $^3J_{N\alpha H-H\alpha}$=6.8 Hz); 5.81 (broad t, 1H, N"H); 4.37 (d, 2H, H-8, $^3J_{8-7}$=7.2 Hz); 4.22 (t, 1H, H-7, $^3J_{7-8}$=7.2 Hz); 4.17 (m, 1H, H-α); 3.26 (q, 4H, H-1α/H-1γ); 2.40 (m, 1H, H-γ); 2.31 (m, 1H, H-γ'); 2.11 (m, 1H, H-β); 2.00 (m, 1H, H-β'); 1.51 (m, 4H, H-2α/H-2γ); 1.23-1.33 (m, H-3α to H-11α/H-3γ to H-11γ); 0.89 (t, 6H, H-12α/H-12γ)

c) Preparation of N',N"-didodecyl-L-glutamide, or compound 22, of formula

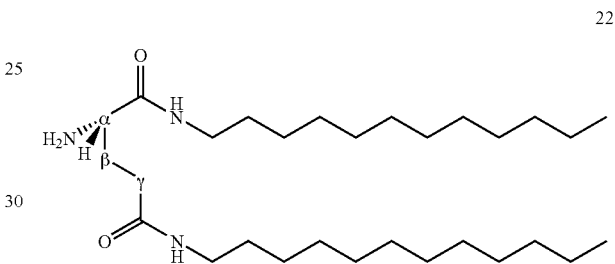

Compound 22 is prepared by following the same operating protocol as that described for the preparation of compound 21 in example 1 above, but using 9.29 g (13.2 mmol; 1 eq.) of compound 20.

5.01 g (10.4 mmol) of compound 22 are thus obtained.
Empirical formula: $C_{29}H_{59}N_3O_2$, M=481.81 g·mol$^{-1}$
Yield: 79%
M.p.: 118° C.
TLC: $R_f$=0.4 eluent: CHCl$_3$/MeOH 9/1 (v/v)
$[\alpha]_D^{20}$+45° (c 0.25, CHCl$_3$)
IR: 3324 cm$^{-1}$ ν(NH$_2$); 1633 cm$^{-1}$ ν(C=O amides)
ESI-MS+: m/z measured at 504.6 [M+Na]$^+$, calculated at 504.5 for $C_{29}H_{59}N_3O_2Na$ $^1$H NMR (CDCl$_3$, 500.13 MHz) δ (ppm): 7.37 (broad t, 1H, N'H); 6.27 (broad t, 1H, N"H); 3.40 (t, 1H, H-α, $^3J_{\alpha-\beta}$=6.8 Hz); 3.21 (m, 4H, H-1α/H-1γ); 2.30 (m, 2H, H-γ); 1.93 (m, 2H, H-β); 1.48 (m, 4H, H-2α/H-2γ); 1.22-1.33 (m, H-3α to H-11α/H-3γ to H-11γ); 0.87 (t, 6H, H-12α/H-12γ, $^3J_{11\alpha-12\alpha}$=$^3J_{11\gamma-12\gamma}$=7.0 Hz)

$^{13}$C NMR (CDCl$_3$, 125.77 MHz) δ (ppm): 174.6 (—CO—N'H); 172.5 (—CO—N"H); 54.1 (C-α); 39.5, 38.9 (C-1α, C-1γ); 33.1 (C-γ); 31.8 (C-10α/C-10γ); 31.6 (C-β); 29.1-29.6 (C-2α, C-4α to C-9α/C-2β, C-4γ to C-9γ); 26.8 (C-3α/C-3γ); 22.5 (C-11α/C-11γ); 14.0 (C-12α/C-12γ)

2.2. Preparation of Compound 24

The coupling of compounds 5 and 22 is carried out by following the same operating protocol as that described for the preparation of compound 23 in example 1 above, but using:

1.04 g (0.84 mmol; 1 eq.) of compound 5
525 μl (3.39 mmol; 4 eq.) of DIC
456.5 mg (3.38 mmol; 4 eq.) of HOBT
610.2 mg (1.27 mmol; 1.5 eq.) of compound 22.
1.10 g (0.65 mmol) of compound 24 are thus obtained.
Empirical formula: C$_{75}$H$_{132}$N$_4$O$_{38}$, M=1697.88 g·mol$^{-1}$
Yield: 77%
M.p.: 160° C. (decomp.)
TLC: R$_f$=0.2 eluent: CHCl$_3$/MeOH/H$_2$O 6/3/0.5 (v/v/v)
[α]$_D^{20}$+69° (c 0.27, DMF)
ES-HRMS (high resolution with detection in the positive mode): m/z measured at 1697.8624 [M+H]$^+$, calculated at 1697.8598 for C$_{75}$H$_{133}$N$_4$O$_{38}$ (deviation: 1.6 ppm)

$^1$H NMR (pyridine-d$_5$, 500.13 MHz) δ (ppm): 9.17 (d, 1H, N$_α$H); 8.82 (t, 1H, NH$_{CD}$); 8.56 (t, 1H, N"H); 8.37 (t, 1H, N'H); 4.94 (m, 1H, H-α); 5.56-5.60 (m), 5.55 (d), 5.46 (d) (6H, H-1$^{II-VII}_{CD}$); 5.43 (d, 1H, H-1$^I_{CD}$); 4.62-4.76 (m, H-3$^{II-VII}_{CD}$); 4.62 (H-3$^I_{CD}$); 4.56-4.64 (m, H-6$^{II-VII}_{CD}$); 4.28-4.53 (m, H-5$^{II-VII}_{CD}$/H-6$^{II-VII}_{CD}$); 4.41 (H-5$^I_{CD}$); 4.14-4.27 (m, H-4$^{II-VII}_{CD}$); 4.19 (H-6$^I_{CD}$); 4.06 (H-6'$^I_{CD}$); 3.98-4.13 (m, H-2$^{II-VII}_{CD}$); 3.92 (dd, 1H, H-2$^I_{CD}$); 3.80 (t, 1H, H-4'$^I_{CD}$); 3.35, 3.30 (m, 4H, H-1α, H-1γ); 2.6-3.0 (m, H-b/H-c); 2.61 (m, H-γ/H-γ'); 2.61 (m, H-β); 2.34 (m, 1H, H-β'); 1.50, 1.47 (m, 4H, H-2α, H-2γ); 1.18 (H-3α/H-3γ); 1.05-1.25 (m, H-4α to H-11α/H-4γ to H-11γ); 0.75 (t, 6H, H-12α/H-12γ)

$^{13}$C NMR (pyridine-d$_5$, 125.77 MHz) δ (ppm): 173.7 (C-a); 173.6 (C-d); 173.2 (—CO—N'H); 172.9 (—CO—N"H); 104.1-104.6 (C-1$^{I-VII}_{CD}$); 85.8 (C-4$^I_{CD}$); 83.8-84.2 (C-4$^{II-VII}_{CD}$); 74.1-75.4 (C-3$^{I-VII}_{CD}$/C-5$^{II-VII}_{CD}$/C-2$^{I-VII}_{CD}$); 72.3 (C-5$^I_{CD}$); 62.7 (C-6$^I_{CD}$); 62.0-62.3 (C-6$^{II-VII}_{CD}$); 41.6 (C-α); 40.3 (C-1α/C-1γ); 33.8 (C-γ); 32.6 (C-10α/C-10γ); 32.1, 32.3 (C-b, C-c); 30.5 (C-2α/C-2γ); 30.1 (C-4α/C-4γ); 30.1-30.7 (C-5α to C-9α/C-5γ to C-9γ); 30.0 (C-β); 27.8, 27.9 (C-3α, C-3γ); 23.4 (C-11α/C-11γ); 14.8 (C-12α/C-12γ)

Example 3

Preparation of N',N"-didodecyl-N$_α$-(6$^I$-amidosuccinyl-6$^I$-deoxy-2$^I$-O-methylhexakis (2$^{II-VII}$,6$^{II-VII}$-di-O-methyl)cyclomaltoheptaose)-L-aspartamide The title compound, or compound 25, of formula:

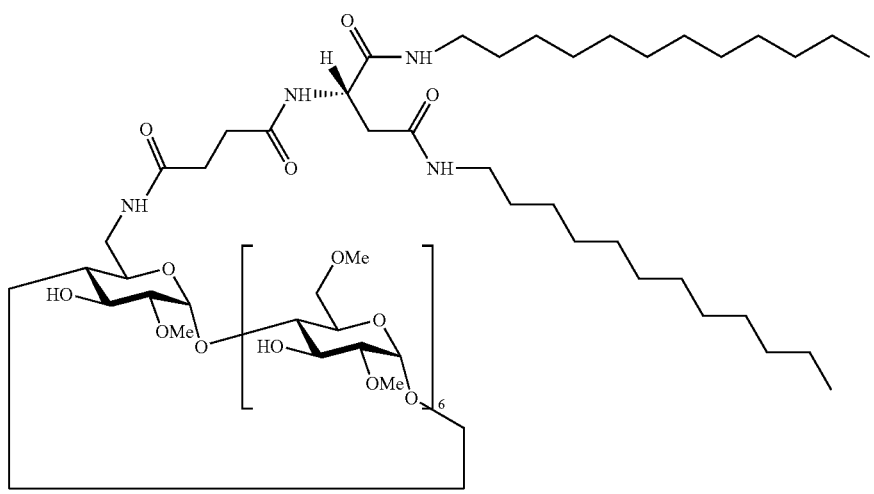

is obtained by coupling 6$^I$-amidosuccinyl-6$^I$-deoxy-per(2,6-di-O-methyl)cyclomaltoheptaose, or compound 9, with compound 21 synthesized in example 1 above.

3.1. Preparation of Compound 9 a) Preparation of 6$^I$-azido-6$^I$-deoxy-2$^I$-O-methylhexakis (2$^{II-VII}$,6$^{II-VII}$-di-O-methyl)cyclomaltoheptaose, or compound 7, of formula

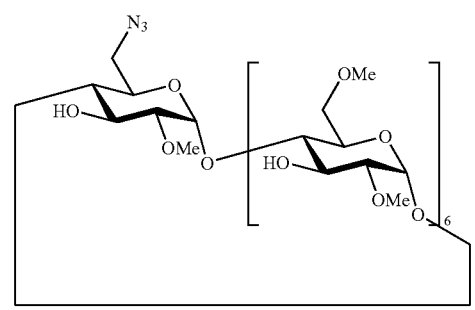

4.45 g (3.84 mmol; 1 eq.) of compound 3 synthesized in example 1 above, dried beforehand in a vacuum oven, are dissolved in 55.7 ml of anhydrous DMF with stirring and under an inert atmosphere, in a dry 250 ml two-necked flask. After having placed the reaction medium in a bath at 8° C., 55.7 ml of anhydrous DMSO are introduced, and then 8.25 g (53.8 mmol; 14 eq.) of barium oxide and 8.50 g (26.9 mmol; 7 eq.) of barium hydroxide octahydrate are successively added. Finally, 6 ml (63.0 mmol) of methyl sulphate, are added and the entire mixture is maintained at 8° C. for 72 hours, with stirring and under an inert atmosphere. 27.5 ml of aqueous ammonia (20% v/v solution) are then slowly added to the grayish suspension obtained. The mixture is then maintained at ambient temperature for 3 hours with stirring. After having allowed the suspension to separate by settling out for 2 hours at 4° C., the supernatant is isolated in a 500 ml round-bottomed flask, concentrated in a rotary evaporator (50° C.) until an oily residue is obtained, and then taken up in 300 ml of dichloromethane. The residual solid from the separation by settling out is taken up with dichloromethane (3×100 ml) and then filtered. The organic phases are combined, washed with a saturated aqueous sodium chloride solution (3×130 ml), and then with water (3×130 ml), dried over sodium sulphate and concentrated in a rotary evaporator (40° C.) until a residual oil is obtained. This residue is precipitated from 250 ml of hexane with stirring. The precipitate is filtered off, washed with hexane and dried in a vacuum oven. 3.59 g (2.67 mmol) of a fine white powder are isolated, corresponding to compound 7, and to per(2,6-di-O-methyl)cyclomaltoheptaose (DIMEB), formed from the β-CD regenerated during the synthesis of compound 3. This mixture will be purified during the subsequent step (preparation of compound 8).

Empirical formula: $C_{55}H_{95}N_3O_{34}$, M=1342.36 g·mol$^{-1}$
Yield: 70%
TLC: $R_f$=0.9 eluent: $CHCl_3$/MeOH 9/1 (v/v)
M.p.: 160° C. (decomp.)
IR: 2101 cm$^{-1}$ $v(N_3)$
ESI-MS+: m/z measured at 1364.5 [M+Na]$^+$, calculated at 1364.6 for $C_{55}H_{95}N_3O_{34}Na$
$^1$H NMR (CDCl$_3$, 500.13 MHz) δ (ppm) 5.25-5.32 (H-1$_{CD}$); 3.99-4.05 (H-3$_{CD}$); 3.88-3.98 (H-5$_{CD}$); 3.70-3.85 (H-6$_{CD}$/H-6'$_{CD}$); 3.60 (OCH$_3$-6$_{CD}$); 3.53-3.68 (H-4$_{CD}$); 3.43 (OCH$_3$-2$_{CD}$); 3.40-3.46 (H-2$_{CD}$)

b) Preparation of 6$^I$-amino-6$^I$-deoxy-2$^I$-O-methylhexakis (2$^{II-VII}$,6$^{II-VII}$-di-O-methyl) cyclomaltoheptaose, or compound 8, of formula

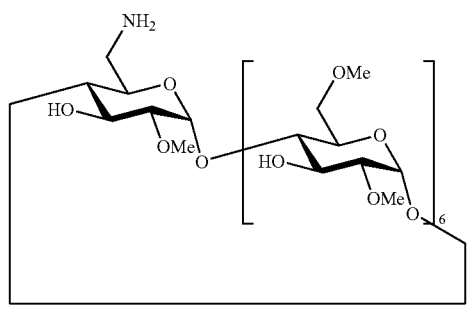

3.51 g (2.61 mmol; 1 eq.) of compound 7 are dissolved in 200 ml of DMF with stirring, in a 500 ml round-bottomed flask. A solution of 2.74 g (10.46 mmol; 4 eq.) of triphenylphosphine (freshly recrystallized from boiling ethanol) dissolved in 10 ml of DMF is added. After stirring at ambient temperature for 2 hours, the reaction medium is cooled to 0° C. in an ice bath and 99 ml of aqueous ammonia (20% v/v solution) are added slowly. The reaction is maintained at ambient temperature for 18 hours with stirring. The solution is then concentrated in a rotary evaporator (40° C.) and the oily residue is taken up in 150 ml of water. The white precipitate formed (mixture of triphenylphosphine and of triphenylphosphine oxide) is filtered off and washed (2×20 ml of water). The filtrate is concentrated under vacuum at 40° C., and then taken up in a minimum of water and adjusted to pH=4.5 by adding a few drops of 1 N HCl. This solution is passed over an ion exchange resin column (V=160 cm$^3$), packed with Lewatit® SP 1080 anionic resin, regenerated beforehand by means of three successive washing cycles alternating 10% aqueous ammonia, water, and 0.1 M of HCl. Compound 8 is strongly retained on the column, while the DIMEB present is eluted with water (5 column volumes). Compound 8 is, in turn, eluted with a 10% aqueous ammonia solution (3 column volumes). The basic eluate is evaporated to dryness in a rotary evaporator (40° C.); the residue is taken up in a minimum of water and then lyophilized. 1.68 g (1.28 mmol) of compound 8 are thus isolated in the form of a white powder.

Empirical formula: $C_{55}H_{97}NO_{34}$, M=1316.36 g·mol$^{-1}$
Estimated yield: 75%
M.p.: 160° C. (decomp.)
TLC: $R_f$=0.4 eluent: $CHCl_3$/MeOH 9/1 (v/v)
IR: absence of band $v(N_3)$
ESI-MS+: m/z measured at 1316.8 [M+H]$^+$, calculated at 1316.6 for $C_{55}H_{98}NO_{34}$
$^1$H NMR (D$_2$O, 500.13 MHz) δ (ppm) 5.24-5.30 (7H, H-1$^{I-VII}$$_{CD}$) 3.92-3.98 (H-3$^{I-VII}$$_{CD}$); 3.80-3.90 (H-5$^{II-VII}$$_{CD}$); 3.72-3.80 (H-6$^{II-VII}$$_{CD}$, H-6'$^{II-VII}$$_{CD}$); 3.71 (H-5$^I$$_{CD}$); 3.61 (OCH$_3$-6$_{CD}$); 3.58-3.65 (H-4$^{II-VII}$$_{CD}$); 3.55 (H-4$^I$$_{CD}$); 3.43 (OCH$_3$-2$_{CD}$); 3.38-3.44 (H-2$^{I-VII}$$_{CD}$); 3.06 (dd, 1H, H-6$^I$$_{CD}$); 2.92 (dd, 1H, H-6'$^I$$_{CD}$)
$^{13}$C NMR (D$_2$O, 125.77 MHz) δ (ppm) 99.3-99.9 (C-1$^{I-VII}$$_{CD}$); 81.5-82.2 (C-4$^{I-VII}$$_{CD}$/C-2$^{I-VII}$$_{CD}$) 72.4-72.7 (C-3$^{I-VII}$$_{CD}$); 70.4-72.7 (C-5$^{I-VII}$$_{CD}$/C-6$^{II-VII}$$_{CD}$) 59.6-59.8 (OCH$_3$-6$_{CD}$); 58.8-59.0 (OCH$_3$-2$_{CD}$); 41.5 (C-6$^I$$_{CD}$)

c) Preparation of 6$^I$-amidosuccinyl-6$^I$-deoxy-2$^I$-O-methylhexakis (2$^{II-VII}$,6$^{II-VII}$-di-O-methyl) cyclomaltoheptaose, or compound 9, of formula

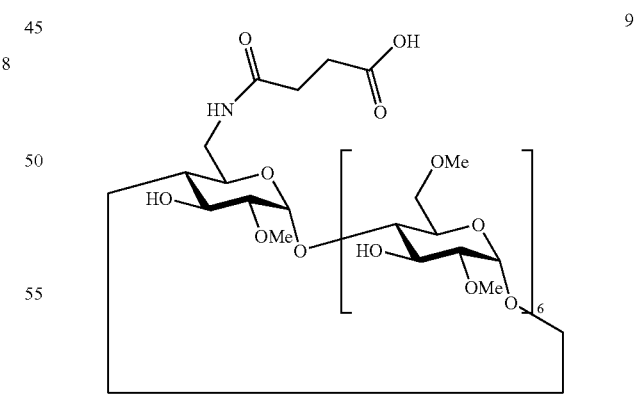

1.093 g (0.83 mmol; 1.1 eq.) of compound 8, lyophilized beforehand, are dissolved in 20 ml of anhydrous DMF with stirring and under an inert atmosphere, in a 100 ml round-bottomed flask. 75.7 mg (0.76 mmol; 1 eq.) of succinic anhydride in solution in 5 ml of anhydrous DMF are then added. The reaction medium is maintained at ambient temperature for 18 hours, with stirring and under an inert atmosphere. The reaction is stopped by adding 100 μl of water. The solvent is evaporated to dryness under vacuum (40° C.) and then the residue is taken up in a minimum of water until complete dissolution. This acidic solution is passed over an ion exchange resin column (V=10 cm$^3$), packed with Lewatit® SP 1080 anionic resin, regenerated beforehand by means of three successive washing cycles alternating 10% aqueous ammonia, water, and 0.1 M HCl. Compound 9 is eluted with water, whereas the excess compound 8 (in the form of an ammonium ion) is strongly retained in the column. The eluate is concentrated in the rotary evaporator (40° C.), and then lyophilized. 821 mg (0.58 mmol) of compound 9 are obtained in the form of a white powder.

Empirical formula: $C_{59}H_{101}NO_{37}$, M=1416.44 g·mol$^{-1}$
Yield: 77%
M.p.: 160° C. (decomp.)
TLC: $R_f$=0.2 eluent: $CHCl_3$/MeOH 9/1 (v/v)
ESI-MS−: m/z measured at 1414.5 for [M−H]$^−$, calculated at 1414.6 for $C_{59}H_{100}NO_{37}$

3.2. Preparation of Compound 25

338.9 mg (0.24 mmol; 1 eq.) of compound 9, lyophilized beforehand, are dissolved in 10 ml of anhydrous DMF with stirring and under an inert atmosphere in a dry 50 ml round-bottomed flask. 149 μl (0.96 mmol; 4 eq.) of DIC and then 129.3 mg (0.96 mmol; 4 eq.) of HOBT, in solution in 5 ml of anhydrous DMF, are successively added. The reaction is then maintained at ambient temperature for 2 hours with stirring and under an inert atmosphere. 169.6 mg (0.36 mmol; 1.5 eq.) of compound 21, dissolved in 15 ml of anhydrous chloroform (freshly distilled over $P_2O_5$), are finally added to the reaction medium. After stirring for 24 hours at ambient temperature and under an inert atmosphere, the reaction is stopped by adding 100 μl of water. The solution is evaporated to dryness under a primary vacuum (40° C.), the residue is taken up in 20 ml of chloroform and the insoluble material is filtered off. The filtrate is concentrated in a rotary evaporator (30° C.) and purified by means of a chromatographic column on Fluka silica gel 60 (elution with 98/2 and then 95/5 (v/v) $CHCl_3$/$CH_3OH$). 267.0 mg (0.14 mmol) of compound 25 are thus isolated in the form of a white powder after lyophilization.

Empirical formula: $C_{87}H_{156}N_4O_{38}$, M=1866.20 g·mol$^{-1}$
Yield: 60%
M.p.: 160° C. (decomp.)
TLC: $R_f$=0.3 eluent: $CHCl_3$/MeOH 8/2 (v/v)
$[\alpha]_D^{20}$+84° (c 0.25, $CHCl_3$)
IR: 3300-3500 cm$^{-1}$ (broad) ν(OH); 1655 cm$^{-1}$ ν(C=O amides)
ES-HRMS (high resolution with detection in the positive mode): m/z measured at 1866.0394 [M+H]$^+$, calculated at 1866.0476 for $C_{87}H_{157}N_4O_{38}$ (deviation: 4.4 ppm); m/z measured at 1888.0214 [M+Na]$^+$, calculated at 1888.0295 for $C_{87}H_{156}N_4O_{38}Na$ (deviation: 4.3 ppm)

$^1$H NMR (CDCl$_3$, 500.13 MHz) δ (ppm): 7.50 (7.58*) (t, 1H, N'H or N"H); 7.44 (7.38*) (d, 1H, N$_\alpha$H); 6.27 (6.21*) (t, 1H, N'H or N"H); 6.11 (t, 1H, NH$_{CD}$); 4.93-5.10 (m, H-1$^{I\text{-}VII}_{CD}$/OH-3$_{CD}$); 4.64 (m, 1H, H-α); 3.88-3.96 (m, H-3$^{I\text{-}VII}_{CD}$); 3.63 (m, OCH$_3$-6$_{CD}$); 3.55-3.77 (m, H-5$^{I\text{-}VII}_{CD}$/H-6$^{I\text{-}VII}_{CD}$/H-6'$^{II\text{-}VII}_{CD}$); 3.40 (m, OCH$_3$-2$_{CD}$); 3.38-3.50 (m, H-4$^{I\text{-}VII}_{CD}$); 3.22-3.32 (m, H-2$^{I\text{-}VII}_{CD}$); 3.19 (m, H-1α/H-1β); 2.88 (dd, 1H, H-β); 2.4-2.7 (m, 4H, H-b/H-c); 2.42 (dd, 1H, H-β'); 1.47 (m, H-2α/H-2β); 1.24-1.31 (m, H-3α to H-11α/H-3β to H-11β); 0.87 (t, 6H, H-12α/H-12β) * conformers $^{13}$C NMR (CDCl$_3$, 125.77 MHz) δ (ppm): 171.9, 171.8, 171.2, 170.2 (4s, —CO—NH); 100.8-101.5 (C-1$^{I\text{-}VII}_{CD}$); 83.0-83.7, 84.9 (C-4$^{I\text{-}VII}_{CD}$); 81.7-82.3 (C-2$^{I\text{-}VII}_{CD}$); 73.0-73.3 (C-3$^{I\text{-}VII}_{CD}$); 69.6-71.6 (C-5$^{I\text{-}VII}_{CD}$); 70.6-71.0 (C-6$^{I\text{-}VII}_{CD}$); 60.2-60.5 (OCH$_3$-6$_{CD}$); 58.9-59.1, 59.5 (OCH$_3$-2$_{CD}$); 50.0 (C-α); 39.7 (C-1α/C-1β); 37.4 (C-β); 31.9 (C-10α/C-10β); 31.1, 31.4 (C-b, C-c); 29.6 (C-2α/C-2β); 29.2-29.7 (C-4α to C-9α/C-4β to C-9β); 26.9 (C-3α/C-3β); 22.6 (C-11α/C-11β); 14.0 (C-12α/C-12β)

Example 4

Preparation of N',N"-didodecyl-N$_\alpha$-(6$^I$-amidosuccinyl-6$^I$-deoxy-2$^I$-O-methylhexakis(2$^{II\text{-}VII}$,6$^{II\text{-}VII}$-di-O-methyl)cyclomaltoheptaose)-L-glutamide The title compound, or compound 26, of formula:

is obtained by coupling compound 9 synthesized in example 3 above, with compound 22 synthesized in example 2 above. For this coupling, the same operating protocol as that described for the preparation of compound 25 in example 3 above is followed, but using:
  804 mg (0.57 mmol; 1 eq.) of compound 9
  355 μl (2.29 mmol; 4 eq.) of DIC
  313.4 mg (2.32 mmol; 4 eq.) of HOBT

Example 5

Preparation of N',N''-didodecyl-$N_\alpha$-($6^I$-amidosuccinyl-$6^I$-deoxy-$2^I,3^I$-di-O-methylhexakis ($2^{II-VII},3^{II-VII},6^{II-VII}$-tri-O-methyl)cyclomaltoheptaose)-L-aspartamide The title compound, or compound 27, of formula:

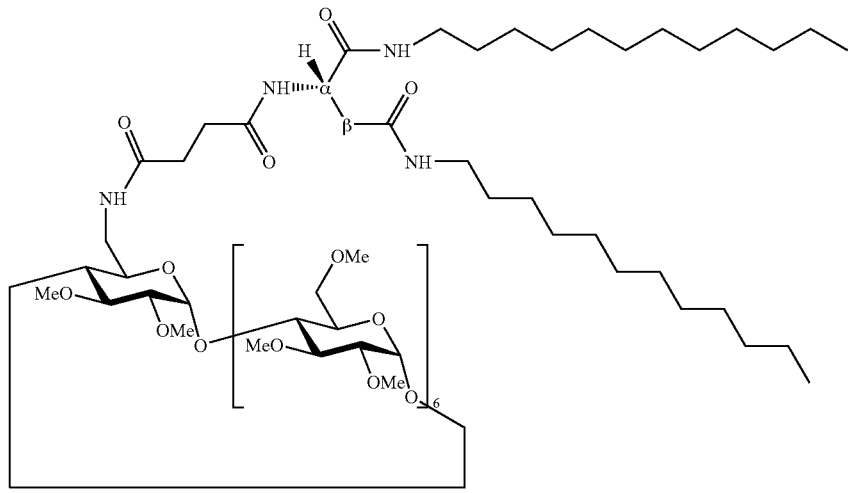

27

411.8 mg (0.855 mmol; 1.5 eq.) of compound 22.
  672.6 g (0.36 mmol) of compound 26 are thus obtained.
  Empirical formula: $C_{88}H_{158}N_4O_{38}$, M=1880.23 g·mol$^{-1}$
  Yield: 63%
  M.p.: 160° C. (decomp.)
  TLC: $R_f$=0.3 eluent: $CHCl_3$/MeOH 8/2 (v/v)
  $[\alpha]_D^{20}$ +98° (c 0.26, $CHCl_3$)
  IR: 3300-3500 cm$^{-1}$ (broad) ν(OH); 1655 cm$^{-1}$ ν(C=O amides)
  ES-HRMS (high resolution with detection in the positive mode): m/z measured at 1902.0529 [M+Na]$^+$, calculated at 1902.0452 for $C_{88}H_{158}N_4O_{38}Na$ (deviation: 4.0 ppm)
  $^1$H NMR (CDCl$_3$, 500.13 MHz) δ (ppm): 7.29 (d, 1H, $N_\alpha H$); 7.04 (broad t, 1H, N'H or N''H); 6.31 (broad t, 1H, $NH_{CD}$); 6.05 (t, 1H, N'H or N''H); 4.94-5.06 (m, 7H, H-$1^{I-VII}{}_{CD}$); 4.31 (m, 1H, H-α); 3.82-4.01 (m, H-$3^{I-VII}{}_{CD}$); 3.63 (m, OCH$_3$-$6_{CD}$); 3.55-3.80 (m, H-$5^{I-VII}{}_{CD}$/H-$6^{I-VII}{}_{CD}$); 3.39-3.52 (m, H-$4^{I-VII}{}_{CD}$); 3.40 (m, OCH$_3$-$2_{CD}$); 3.15-3.33 (m, H-$2^{I-VII}{}_{CD}$); 3.21 (m, H-1α/H-1γ); 2.5-2.6 (m, 4H, H-b/H-c); 2.46 (m, 1H, H-γ); 2.29 (m, 1H, H-γ'); 2.08 (m, 1H, H-β); 1.99 (m, 1H, H-β'); 1.49 (m, 4H, H-2α/H-2γ); 1.24-1.32 (m, H-3 to H-11α/H-3γ to H-11γ); 0.88 (t, 6H, H-12α/H-12γ)
  $^{13}$C NMR (CDCl$_3$, 125.77 MHz) δ (ppm) 172.9, 172.1, 172.0, 170.9 (4s, —CO—NH); 100.8-101.5 (C-$1^{I-VII}{}_{CD}$); 83.0-83.7, 85.0 (C-$4^{I-VII}{}_{CD}$); 81.7-82.4 (C-$2^{I-VII}{}_{CD}$); 73.0-73.4 (C-$3^{I-VII}{}_{CD}$); 69.7-71.7 (C-$5^{I-VII}{}_{CD}$); 70.5-71.4 (C-$6^{I-VII}{}_{CD}$); 60.1-60.5 (OCH$_3$-$6_{CD}$); 58.9-59.2, 59.4 (OCH$_3$-$2_{CD}$); 52.8 (C-α); 39.7, 39.8 (2s, C-1α, C-1γ); 32.9 (C-γ); 31.9 (C-10α/C-10γ); 31.4 (C-b/C-c); 29.4 (C-2α/C-2γ); 29.2-29.7 (C-4α to C-9α/C-4γ to C-9γ); 29.1 (C-β); 27.0, 26.9 (2s, C-3α, C-3γ); 22.6 (C-11α/C-11γ); 14.0 (C-12α/C-12γ)

is obtained by coupling $6^I$-amidosuccinyl-$6^I$-deoxy-$2^I,3^I$-di-O-methylhexakis($2^{II-VII},3^{II-VII},6^{II-VII}$-tri-O-methyl)cyclomaltoheptaose, or compound 13, with compound 21 synthesized in example 1 above.

5.1. Preparation of Compound 13 a) Preparation of $6^I$-azido-$6^I$-deoxy-$2^I3^I$-di-O-methylhexakis($2^{II-VII},3^{II-VII},6^{II-VII}$-tri-O-methyl)cyclomaltoheptaose, or compound 11, of formula

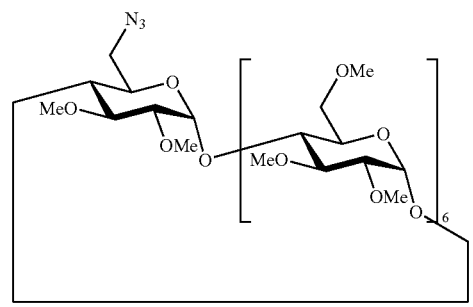

11

6.2 g (0.26 mol; ~100 eq.) of sodium hydride (coated with 60% m/m oil, i.e. 10 g of coated product) are introduced into a dry 500 ml two-necked flask. The product is placed under an inert atmosphere, washed with anhydrous hexane (2×50 ml) so as to remove the coating, and then dried under a stream of nitrogen. The sodium hydride is then suspended in 130 ml of anhydrous DMF with stirring. 3.01 g (2.60 mmol; 1 eq.) of compound 3 synthesized in example 1 above, dried beforehand in a vacuum oven, are dissolved in 200 ml of anhydrous DMF with stirring and under an inert atmosphere, and then added to the reaction medium. The mixture is cooled to 0° C. in an ice bath then 30 ml (0.48 mol; ~185 eq.) of methyl iodide are added. The reaction is maintained at ambient temperature for 24 hours with stirring. The reaction medium is then filtered and the filtrate is concentrated in a rotary evaporator (40° C.). The oily residue is taken up in a minimum of water and then extracted with chloroform (4×40 ml). The organic phase is washed with water (2×50 ml), dried over sodium sulphate, filtered, and concentrated in a rotary evaporator (40° C.). The oily residue is taken up in a minimum of water, the insoluble material is filtered off and the solution is lyophilized. 3.38 g (2.35 mmol) of a white powder are isolated, corresponding to compound 11, and to per(2,3,6-tri-O-methyl)cyclomaltoheptaose (TRIMEB), formed from the β-CD generated during the synthesis of compound 3. This mixture will be purified during the subsequent step (preparation of compound 12).

Empirical formula: $C_{62}H_{109}N_3O_{34}$, M=1440.55 g·mol$^{-1}$
Yield: 90%
M.p.: 160° C. (decomp.)
TLC: $R_f$=0.9 eluent: $CHCl_3$/MeOH 9/1 (v/v)
IR: 2096 cm$^{-1}$ $v(N_3)$
ES-MS+: m/z measured at 1462.8 [M+Na]$^+$, calculated at 1462.7 for $C_{62}H_{109}N_3O_{34}Na$
$^1$H NMR (CDCl$_3$, 500.13 MHz) δ (ppm): 5.31-5.36 (H-1$_{CD}$); 3.88-3.96 (H-5$_{CD}$/H-6$_{CD}$); 3.69-3.84 (H-4$_{CD}$/H-6'$_{CD}$/H-3$_{CD}$); 3.65 (OCH$_3$-6$_{CD}$); 3.56 (OCH$_3$-3$_{CD}$); 3.43 (OCH$_3$-2$_{CD}$); 3.38-3.42 (H-2$_{CD}$)

b) Preparation of 6$^I$-amino-6$^I$-deoxy-2$^I$,3$^I$-di-O-methylhexakis(2$^{II-VII}$,3$^{II-VII}$,6$^{II-VII}$-tri-O-methyl)cyclomaltoheptaose, or compound 12, of formula

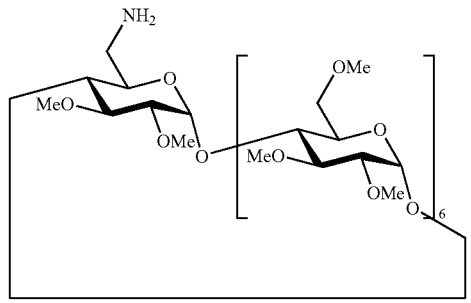

12

3.37 g (2.34 mmol; 1 eq.) of compound 11 are dissolved in 180 ml of DMF with stirring, in a 500 ml round-bottomed flask. A solution of 2.46 g (9.38 mmol; 4 eq.) of triphenylphosphine (freshly recrystallized from boiling ethanol) dissolved in 10 ml of DMF is added. After stirring at ambient temperature for 2 hours, the reaction medium is cooled to 0° C. in an ice bath and 88.5 ml of aqueous ammonia (20% v/v solution) are slowly added. The reaction is maintained at ambient temperature for 18 hours with stirring. The solution is then concentrated in a rotary evaporator (40° C.) and the oily residue is taken up in 140 ml of water. The white precipitate formed (mixture of triphenylphosphine and of triphenylphosphine oxide) is filtered off and washed (2×20 ml of water). The filtrate is concentrated under vacuum at 40° C., then taken up in a minimum of water and adjusted to pH=4.5 by adding a few drops of 1 N HCl. This solution is passed over an ion exchange resin column (V=160 cm$^3$), packed with Lewatit® SP 1080 anionic resin, regenerated beforehand by means of three successive washing cycles alternating 10% aqueous ammonia, water, and 0.1 M HCl. Compound 12 is strongly retained on the column, whereas the TRIMEB present is eluted with water (5 column volumes). Compound 12 is, in turn, eluted with a 10% aqueous solution (3 column volumes). The basic eluate is evaporated to dryness under vacuum (40° C.); the residue is taken up in a minimum of water and then lyophilized. 1.85 g (1.31 mmol) of compound 12, are thus isolated in the form of a white powder.

Empirical formula: $C_{62}H_{111}NO_{34}$, M=1414.55 g·mol$^{-1}$
Estimated yield: 86%
M.p.: 160° C. (decomp.)
TLC: $R_f$=0.7 eluent: $CHCl_3$/MeOH 8/2 (v/v)
IR: Absence of the band $v(N_3)$
ES-MS+: m/z measured at 1414.8 [M+H]$^+$, calculated at 1414.7 for $C_{62}H_{112}NO_{34}$
$^1$H NMR (D$_2$O, 500.13 MHz) δ (ppm) 5.36 (d, 1H, H-1$^I_{CD}$, $^3J^I_{1-2}$=3.6 Hz); 5.30-5.35 (m, 6H, H-1$^{II-VII}_{CD}$); 3.86-3.96 (m, H-5$^{II-VII}_{CD}$); 3.87-3.92 (m, H-6$^{II-VII}_{CD}$); 3.83 (H-5$^I_{CD}$); 3.75-3.83 (m, H-4$^{II-VII}_{CD}$); 3.76 (H-3$^I_{CD}$); 3.69-3.79 (m, H-3$^{II-VII}_{CD}$); 3.71 (H-4$^I_{CD}$); 3.65-3.73 (m, H-6$^{II-VII}_{CD}$); 3.64-3.66 (m, OCH$_3$-6$_{CD}$); 3.55-3.57 (m, OCH$_3$-3$_{CD}$); 3.43 (H-2$^I_{CD}$); 3.42-3.43 (m, OCH$_3$-2$_{CD}$); 3.36-3.44 (m, H-2$^{II-VII}_{CD}$); 3.05 (dd, 1H, H-6$^I_{CD}$, $^3J^I_{6-5}$=5.5 Hz, $^3J^I_{6-6'}$=14.2 Hz); 2.96 (dd, 1H, H-6'$^I_{CD}$, $^3J^I_{6'-5}$=3.0 Hz, $^3J^I_{6'-6}$=14.2 Hz)
$^{13}$C NMR (D$_2$O, 125.77 MHz) δ (ppm) 97.1-97.8 (C-1$^{I-VII}_{CD}$); 80.9-81.6 (C-3$^{I-VII}_{CD}$); 80.2-80.6 (C-2$^{I-VII}_{CD}$); 76.7-78.6 (C-4$^{I-VII}_{CD}$); 71.0-71.4 (C-6$^{II-VII}_{CD}$); 70.7-71.7 (C-5$^{I-VII}_{CD}$); 59.8-60.4 (OCH$_3$-6$_{CD}$); 58.3-59.0 (OCH$_3$-3$_{CD}$/OCH$_3$-2$_{CD}$); 41.6 (C-6$^I_{CD}$)

c) Preparation of 6$^I$-amidosuccinyl-6$^I$-deoxy-2$^I$,3$^I$-di-O-methylhexakis(2$^{I-VII}$,3$^{I-VII}$,6$^{II-VII}$-tri-O-methyl)cyclomaltoheptaose, or compound 13, of formula

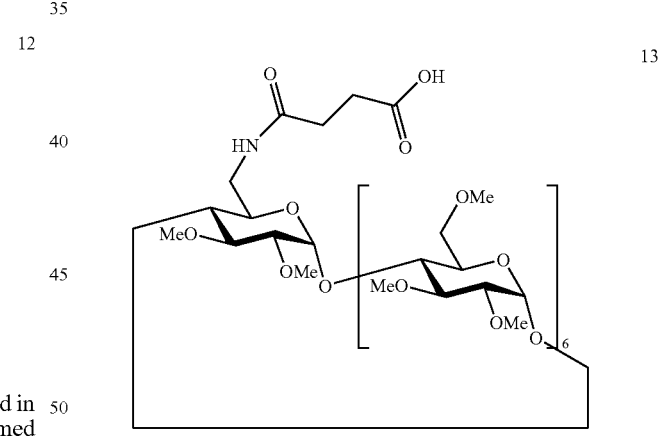

13

996.7 mg (0.70 mmol; 1 eq.) of compound 12, lyophilized beforehand, are dissolved in 20 ml of anhydrous DMF with stirring and under an inert atmosphere, in a 100 ml round-bottomed flask. 105.7 mg (1.06 mmol; 1.5 eq.) of succinic anhydride in solution in 5 ml of anhydrous DMF are then added. The reaction medium is maintained at ambient temperature for 18 hours with stirring and under an inert atmosphere. The reaction is stopped by adding 100 μl of water. The solvent is eliminated in a rotary evaporator (40° C.) and the residue is then taken up in 50 ml of chloroform. The insoluble material (succinic acid) is filtered over a 0.22 μm Teflon® filter and the chloroform is evaporated to dryness under vacuum (40° C.). The residue is taken up in a minimum of water and lyophilized. 1.03 g (0.68 mmol) of compound 13 are obtained in the form of a white powder.

Empirical formula: $C_{66}H_{115}NO_{37}$, M=1514.62 g·mol$^{-1}$
Yield: 96%
M.p.: 160° C. (decomp.)
TLC: $R_f$=0.6 eluent: $CH_2Cl_2$/MeOH 9/1 (v/v)
IR: 1733 cm$^{-1}$ ν(C=O acid); 1676 cm$^{-1}$ ν(C=O amide)
ES-MS+: m/z measured at 1536.9 [M+Na]$^+$, calculated at 1536.7 for $C_{66}H_{115}NO_{37}Na$ $^1$H NMR (CDCl$_3$, 500.13 MHz) δ (ppm) 6.40 (t, 1H, NH$_{CD}$, $^3J_{NH-6}{}^I$=5.6 Hz); 5.24, 5.22, 5.14, 5.11, 5.07, 5.07 (6d, H-1$^{II-VII}{}_{CD}$, $^3J_{1-2}$=3.7 Hz); 5.08 (d, H-1$^I{}_{CD}$, $^3J_{1}{}^I{}_{-2}{}^I$=3.7 Hz); 3.85-3.95 (m, H-6$^{II-VII}{}_{CD}$); 3.87 (H-5$^I{}_{CD}$); 3.86, 3.73, 3.78, 3.87, 3.82, 3.79 (H-5$^{II-VII}{}_{CD}$); 3.77 (H-6$^I{}_{CD}$); 3.62-3.68 (m, OCH$_3$-6$_{CD}$); 3.63, 3.63, 3.63, 3.60, 3.62, 3.70 (H-4$^{II-VII}{}_{CD}$); 3.55-3.65 (H-6$^{II-VII}{}_{CD}$); 3.57 (H-3$^I{}_{CD}$); 3.46, 3.57, 3.56, 3.50, 3.50, 3.44 (H-3$^{II-VII}{}_{CD}$); 3.49-3.53 (m, OCH$_3$-3$_{CD}$); 3.38-3.42 (m, OCH$_3$-2$_{CD}$); 3.36 (H-4$^I{}_{CD}$); 3.35 (H-6$^I{}_{CD}$); 3.20, 3.19, 3.18, 3.18, 3.18, 3.18 (H-2$^{II-VII}{}_{CD}$); 3.18 (H-2$^I{}_{CD}$); 2.74, 2.65, 2.49 (4H, H-b/H-c, syst. AA'B)

$^{13}$C NMR (CDCl$_3$, 125.77 MHz) δ (ppm) 174.5 (C-d); 172.7 (C-a); 98.7-99.9 (7s, C-1$^{I-VII}{}_{CD}$); 82.0-82.9 (C-3$^{I-VII}{}_{CD}$/C-2$^{I-VII}{}_{CD}$); 79.6-81.4 (C-4$^{I-VII}{}_{CD}$); 71.5-72.2 (C-6$^{II-VII}{}_{CD}$); 70.7-71.9 (C-5$^{I-VII}{}_{CD}$); 61.7-62.3 (OCH$_3$-6$_{CD}$); 58.9-60.1 (OCH$_3$-3$_{CD}$/OCH$_3$-2$_{CD}$); 42.0 (C-6$^I{}_{CD}$); 31.5, 30.5 (C-b, C-c)

5.2. Preparation of Compound 27

1.01 g (0.67 mmol; 1 eq.) of compound 13, lyophilized beforehand, are dissolved in 15 ml of anhydrous DMF with stirring and under an inert atmosphere, in a dry 100 ml three-necked flask. 415 μl (2.68 mmol; 4 eq.) of DIC and then 361.4 mg (2.68 mmol; 4 eq.) of HOBT, in solution in 5 ml of anhydrous DMF, are added successively. The reaction is then maintained at ambient temperature for 2 hours with stirring and under an inert atmosphere.

376.1 mg (0.80 mmol; 1.2 eq.) of compound 21, dissolved in 20 ml of anhydrous chloroform (freshly distilled over P$_2$O$_5$), are added to the reaction medium. After stirring for 24 hours at ambient temperature and under an inert atmosphere, the reaction is stopped by adding 100 μl of water. The solution is evaporated to dryness under a primary vacuum (40° C.), the residue is taken up in 20 ml of chloroform and the insoluble material is filtered off. The filtrate is concentrated in a rotary evaporator (30° C.) and purified by means of a chromatographic column on Fluka silica gel 60 (elution with 99/1 then 98/2 then 95/5 (v/v) CHCl$_3$/CH$_3$OH). 605 mg (0.31 mmol) of compound 27 are thus isolated in the form of a white powder after lyophilization.

Empirical formula: $C_{94}H_{170}N_4O_{38}$, M=1964.39 g·mol$^{-1}$
Yield: 46%
M.p.: 160° C. (decomp.)
TLC: $R_f$=0.4 eluent: CHCl$_3$/MeOH 95/5 (v/v)
$[α]_D^{20}$+107° (c 0.27, CHCl$_3$)
IR: Absence of band ν(OH); 1651 cm$^{-1}$ ν(C=O amides)
ES-HRMS (high resolution with detection in the positive mode): m/z measured at 1986.1432 [M+Na]$^+$, calculated at 1986.1391 for $C_{94}H_{170}N_4O_{38}Na$ (deviation: 2.1 ppm)

$^1$H NMR (CDCl$_3$, 500.13 MHz) δ (ppm): 7.56 (t, 1H, N'H or N"H); 7.45 (d, 1H, N$_α$H); 6.37 (t, 1H, N'H or N"H); 6.16 (t, 1H, NH$_{CD}$); 5.08-5.17 (m, H-1$^{I-VII}{}_{CD}$); 4.65 (m, H-α); 3.70-3.90 (H-5$^{I-VII}{}_{CD}$/H-6$^{I-VII}{}_{CD}$); 3.4-3.7 (H-4$^{I-VII}{}_{CD}$/H-6$^{I-VII}{}_{CD}$); 3.63 (m, OCH$_3$-6$_{CD}$); 3.42-3.56 (H-3$^{I-VII}{}_{CD}$); 3.50 (m, OCH$_3$-3$_{CD}$); 3.38 (m, OCH$_3$-2$_{CD}$); 3.36 (H-4$^I{}_{CD}$); 3.12-3.24 (H-2$^{I-VII}{}_{CD}$); 3.18 (m, H-1α/H-1β); 2.87 (dd, 1H, H-β); 2.4-2.7 (m, 4H, H-b/H-c); 2.43 (dd, 1H, H-β'); 1.47 (m, H-2α/H-2β); 1.23-1.31 (m, H-3α to H-11α/H-3β to H-11β); 0.87 (t, 6H, H-12α/H-12β)

$^{13}$C NMR (CDCl$_3$, 125.77 MHz) δ (ppm): 170.3, 171.1, 171.8, 171.9 (4s, —CO—NH); 98.0-99.2 (C-1$^{I-VII}{}_{CD}$); 79.1-82.3 (C-3$^{I-VII}{}_{CD}$/C-2$^{I-VII}{}_{CD}$/C-4$^{I-VII}{}_{CD}$); 70.5-71.5 (C-6$^{II-VII}{}_{CD}$/C-5$^{II-VII}{}_{CD}$); 70.0 (C-5$^I{}_{CD}$); 61.0-61.6 (OCH$_3$-6$_{CD}$); 58.0-59.5 (OCH$_3$-2$_{CD}$/OCH$_3$-3$_{CD}$); 49.9 (C-α); 40.1 (C-6$^I{}_{CD}$); 39.6 (C-1α/C-1β); 37.3 (C-β); 31.8 (C-10α/C-10β); 31.0, 31.4 (C-b, C-c); 29.0-29.7 (C-4α to C-9α/C-4β to C-9β); 26.8 (C-3α/C-3β); 22.5 (C-11α/C-11β); 14.0 (C-12α/C-12β)

Example 6

Preparation of N'-dodecyl-N"-hexadecyl-N$_α$-(6$^I$-amidosuccinyl-6$^I$-deoxy-cyclomaltoheptaose)-L-aspartamide The title compound, or compound 33, of formula:

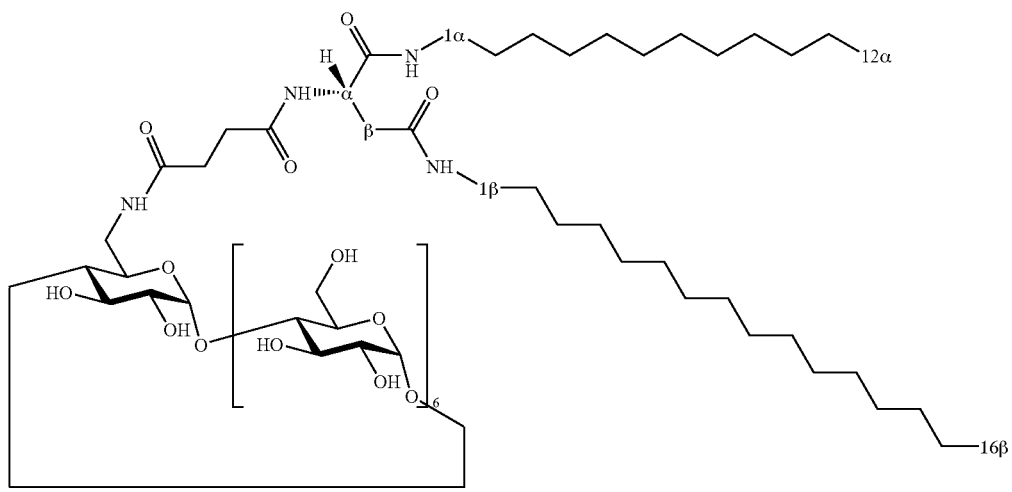

is obtained by coupling compound 5 synthesized in example 1 above with N'-dodecyl-N''-hexadecyl-L-aspartamide, or compound 32.

6.1. Preparation of Compound 32 a) Preparation of N'-dodecyl-N''-(tert-butyloxycarbonyl)-$N_\alpha$-(9-fluorenylmethoxycarbonyl)-L-aspartamide, or compound 29, of formula

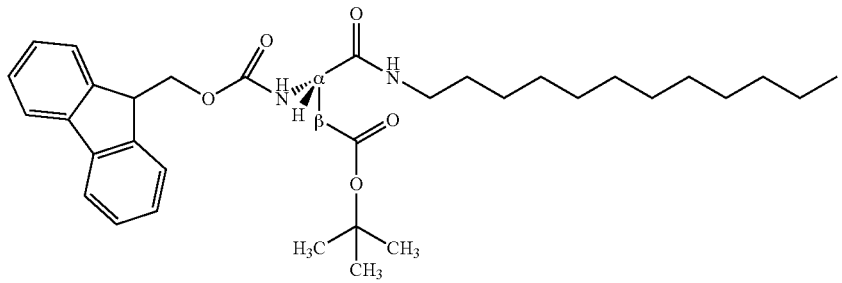

29

504.7 mg (1.23 mmol; 1 eq.) of N''-(tert-butyloxycarbonyl)-$N_\alpha$-(9-fluorenylmethoxycarbonyl)-L-aspartic acid (Fluka) are dissolved in 5 ml of anhydrous DMF with stirring and under an inert atmosphere, in a dry 100 ml round-bottomed flask. 285 µl (1.84 mmol; 1.5 eq.) of DIC and then 249.5 mg (1.85 mmol; 1.5 eq.) of HOBT dissolved in 1 ml of anhydrous DMF, are successively added. The reaction is then maintained at ambient temperature for 2 hours with stirring and under an inert atmosphere. 344.2 mg (1.86 mmol; 1.5 eq.) of dodecylamine, in solution in 20 ml of anhydrous chloroform, are finally added to the reaction medium. After 18 hours of stirring at ambient temperature and under an inert atmosphere, the reaction is stopped by adding 100 µl of water. The solution is evaporated to dryness under a primary vacuum (40° C.), the residue is taken up in 20 ml of chloroform and the insoluble material is filtered off. The filtrate is concentrated in a rotary evaporator (30° C.) and purified by means of a chromatographic column on Fluka silica gel 60 (elution with $CHCl_3$+AcOH (0.2%)). The eluate is evaporated to dryness and the residue is taken up in a minimum of methanol. Compound 29 is then precipitated by adding 50 ml of water. The solid is filtered off over sintered glass and washed with water. After drying overnight in a vacuum oven, 619.4 mg (1.07 mmol) of compound 29 are isolated in the form of a white powder.

Empirical formula: $C_{35}H_{50}N_2O_5$, M=578.79 g·mol$^{-1}$

Yield: 87%

IR: 3349 cm$^{-1}$ (broad) ν(NH-amide); 1744 cm$^{-1}$ ν(C=O ester); 1701 cm$^{-1}$ ν(C=O carbamate); 1646 cm$^{-1}$ ν(C=O amide)

ESI-MS+: m/z measured at 601.5 [M+Na]$^+$, calculated at 601.4 for $C_{35}H_{50}N_2O_5Na$ $^1$H NMR (CDCl$_3$, 500.13 MHz) δ (ppm): 7.77 (d, 2H, H-4/H-4', $^3J_{4-3}$=$^3J_{4'-3'}$=7.5 Hz); 7.62 (d, H-1, $^3J_{1-2}$=7.5 Hz); 7.61 (d, H-1', $^3J_{1'-2'}$=7.5 Hz); 7.41 (t, 2H, H-3/H-3', $^3J_{3-2}$=$^3J_{3-4}$=$^3J_{3'-2'}$=$^3J_{3'-4'}$=7.5 Hz); 7.32 (t, 2H, H-2/H-2', $^3J_{2-1}$=$^3J_{2-3}$=$^3J_{2'-1'}$=$^3J_{2'-3'}$=7.5 Hz); 6.09 (d, 1H, $N_\alpha H$, $^3J_{N\alpha H-\alpha}$=8.3 Hz); 5.62 (broad t, 1H, N'H); 4.48 (m, 1H, H-α); 4.40 (dd, 1H, H-8); 4.32 (dd, 1H, H-8'); 4.23 (t, 1H, H-7); 3.24 (m, 2H, H-1α); 2.87 (dd, 1H, H-β, $^3J_{\beta-\beta'}$=15.5 Hz, $^3J_{\beta-\alpha}$=5.1 Hz); 2.71 (dd, 1H, H-β', $^3J_{\beta'-\beta}$=15.5 Hz, $^3J_{\beta'-\alpha}$=4.3 Hz); 1.49 (s, 3×CH$_3$ tBu); 1.47 (m, H-2α); 1.24-1.32 (m, 18H, H-3α to H-11α); 0.89 (t, 3H, H-12α, $^3J_{12\alpha-11\alpha}$=6.8 Hz)

$^{13}$C NMR (CHCl$_3$, 125.77 MHz) δ (ppm): 170.7 (—CO—N'H); 170.3 (—CO-OtBu); 156.9 (C-10); 144.6, 144.5 (C-5, C-5'); 141.9 (C-6/C-6'); 128.4 (C-3/C-3'); 127.7 (C-2/C-2'); 125.9 (C-1/C-1'); 120.6 (C-4/C-4'); 83.0 (—C-tBu); 67.9 (C-8); 52.1 (C-α); 47.8 (C-7); 40.3 (C-1α); 38.8 (C-β); 32.6 (C-10α); 29.9-30.4, C-4α to C-9α); 30.0 (C-2α); 28.6 (3×CH3 tBu); 27.6 (C-3α); 23.4 (C-11α); 14.8 (C-12α)

b) Preparation of N'-dodecyl-$N_\alpha$-(9-fluorenyl-methoxycarbonyl)-L-aspartamide, or compound 30, of formula

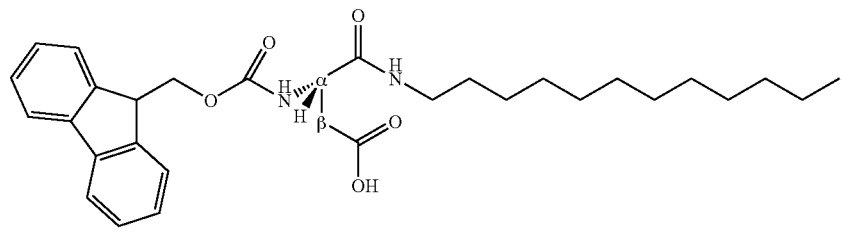

30

542.6 mg (0.94 mmol; 1 eq.) of compound 29 are dissolved in 10 ml of a 20% (v/v) solution of trifluoroacetic acid in dichloromethane, in a 50 ml round-bottomed flask. The reaction medium is maintained at ambient temperature for 3 hours with stirring. The solution is then evaporated to dryness under a primary vacuum (30° C.). The residue is taken up in a minimum of ethyl acetate and precipitated by adding 40 ml of petroleum ether. After having allowed the suspension to separate by settling out at 2 hours at 4° C., the precipitate is filtered off over sintered glass and then dried overnight in a vacuum oven. 461.7 mg (0.88 mmol) of compound 30 are obtained in the form of a white-coloured powder.

Empirical formula: $C_{31}H_{42}N_2O_5$, M=522.68 g·mol$^{-1}$
Yield: 94%
M.p.: 155° C.
TLC: $R_f$=0.1 eluent: $CHCl_3$/MeOH 9/1 (v/v)
IR: 3306 cm$^{-1}$ (broad) ν(NH-amide); 1703 cm$^{-1}$ (2s) ν(C═O acid) and ν(C═O carbamate); 1645 cm$^{-1}$ ν(C═O amide)
ESI-MS+: m/z measured at 545.5 [M+Na]$^+$, calculated at 545.3 for $C_{31}H_{42}N_2O_5Na$
$^1$H NMR (DMSO-d6, 500.13 MHz) δ (ppm): 12.8 (broad s-COOH); 7.99 (d, 2H, H-4/H-4', $^3J_{4-3}$=$^3J_{4'-3'}$=7.5 HZ); 7.92 (broad t, 1H, N'H); 7.80 (d, 2H, H-1/H-1', $^3J_{1-2}$=$^3J_{1'-2'}$=7.5 Hz); 7.64 (d, 1H, N$_\alpha$H, $^3J_{N\alpha H-\alpha}$=8.3 Hz); 7.51 (t, 2H, H-3/H-3', $^3J_{3-2}$=$^3J_{3-4}$=$^3J_{3'-2'}$=$^3J_{3'-4'}$=7.5 Hz); 7.42 (t, 2H, H-2/H-2', $^3J_{2-1}$=$^3J_{2-3}$=$^3J_{2'-1'}$=$^3J_{2'-3'}$=7.5 Hz); 4.46 (dt, 1H, H-α, $^3J_{\alpha-N\alpha H}$=$^3J_{\alpha-\beta'}$=8.3 Hz, $^3J_{\alpha-\beta}$=5.2 Hz); 4.34 (H-8); 4.31 (H-7); 3.12 (m, 2H, H-1α); 2.67 (dd, 1H, H-β, $^3J_{\beta-\beta'}$=15 Hz, $^3J_{\beta-\alpha}$=5.2 Hz); 2.57 (dd, 1H, H-β', $^3J_{\beta'-\beta}$=15 Hz, $^3J_{\beta'-\alpha}$=8.3 Hz); 1.45 (m, 2H, H-2α); 1.28-1.36 (m, 18H, H-3α to H-11α); 0.94 (t, 3H, H-12α, $^3J_{12\alpha-11\alpha}$=6.8 Hz)
$^{13}$C NMR (DMSO-d6, 125.77 MHz) δ (ppm): 173.1 (—COOH); 168.8 (—CO—N'H); 155.7 (C-10); 143.7 (C-5/C-5'); 140.7 (C-6/C-6'); 127.6 (C-3/C-3'); 127.0 (C-2/C-2'); 125.2 (C-1/C-1'); 120.1 (C-4/C-4'); 65.7 (C-8); 50.7 (C-α); 46.6 (C-7); 38.6 (C-1α); 37.0 (C-β); 31.3 (C-10α); 28.6-29.1 (C-2α, C-4α to C-9α); 26.3 (C-3α); 22.1 (C-11α); 13.9 (C-12α)

c) Preparation of N'-dodecyl-N''-hexadecyl-N$_\alpha$-(9-fluorenylmethoxycarbonyl)-L-aspartamide, or compound 31, of formula

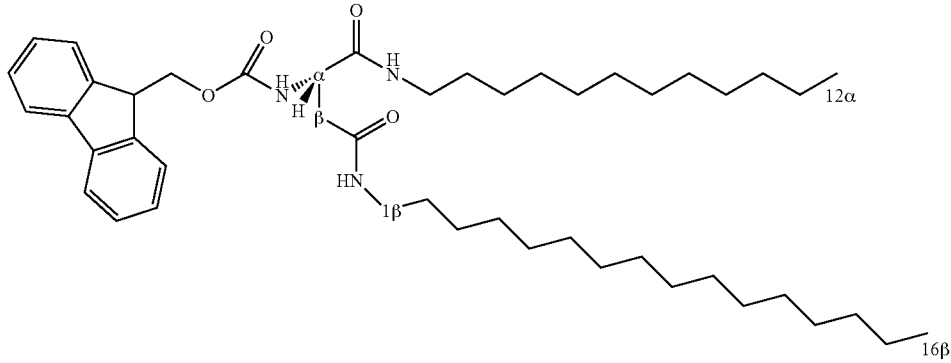

396.0 mg (0.76 mmol; 1 eq.) of compound 30 are dissolved in 5 ml of anhydrous DMF with stirring and under an inert atmosphere, in a dry 50 ml round-bottomed flask. 176 μl (1.14 mmol; 1.5 eq.) of DIC and then 155.2 mg (1.15 mmol; 1.5 eq.) of HOBT dissolved in 1 ml of anhydrous DMF, are successively added. The reaction is then maintained at ambient temperature for 2 hours with stirring and under an inert atmosphere. 276.9 mg (1.15 mmol; 1.5 eq.) of hexadecylamine, in solution in 20 ml of anhydrous chloroform, are added to the reaction medium and the entire mixture is left at ambient temperature for 24 hours, with stirring and under an inert atmosphere (an abundant precipitate rapidly forms). The mixture is then concentrated in a rotary evaporator (40° C.) and taken up in DMF. The pasty solid is filtered off over sintered glass and washed, first with DMF, and then with ether. After drying overnight in a vacuum oven, 335.7 mg (0.46 mmol) of compound 31, are isolated in the form of a fine white powder.

Empirical formula: $C_{47}H_{75}N_3O_4$, M=746.13 g·mol$^{-1}$
Yield: 61%
TLC: $R_f$=0.85 eluent: $CHCl_3$/MeOH 95/5 (v/v)

d) Preparation of N'-dodecyl-N''-hexadecyl-L-aspartamide, or compound 32, of formula

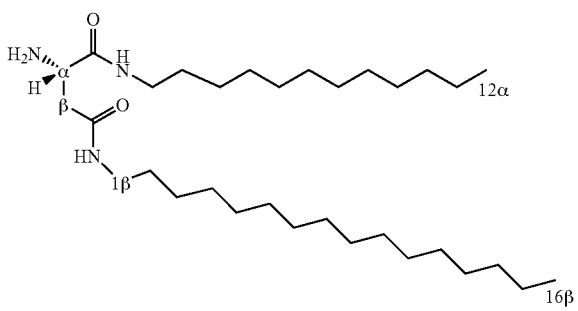

330 mg (0.44 mmol; 1 eq.) of compound 31 are dissolved in 10 ml of a 20% (v/v) solution of piperidine in chloroform, in a 50 ml round-bottomed flask. The solution is heated for a few minutes at 40° C. The reaction medium, first heterogeneous because of the poor solubility of the starting product in chloroform, rapidly becomes clear. The solution is then evaporated to dryness, under a primary vacuum (40° C.), so as to remove the maximum amount of piperidine (bp 101-106° C.). The solid residue is taken up in 1 ml of chloroform so as to then be precipitated in 100 ml of hexane with stirring. After having allowed the suspension to separate by settling out for 2 hours at 4° C., the precipitate is recovered by centrifugation (10 000 rpm, 20 min). The solid is dried, and then a final step consisting of recrystallization from methanol (dissolution in a minimum of boiling methanol, filtration of the insoluble material under hot conditions and recrystallization at 4° C.) makes it possible to isolate by filtration, and after drying overnight in a vacuum oven, 196 mg (0.37 mmol) of compound 32 in the form of a pulverulent white powder.

Empirical formula: $C_{32}H_{65}N_3O_2$, M=523.89 g·mol$^{-1}$

Yield: 84%

M.p.: 104° C.

TLC: $R_f$=0.5 eluent: $CHCl_3$/MeOH 9/1 (v/v)

IR: 3315 cm$^{-1}$ (broad) ν(NH-amide) and ν($NH_2$); 1631 cm$^{-1}$ ν(C=O amide)

ESI-MS+: m/z measured at 524.6 [M+Na]$^+$, calculated at 524.5 for $C_{32}H_{66}N_3O_2$ $^1$H NMR ($CDCl_3$, 500.13 MHz) δ (ppm): 7.50 (broad t, 1H, N'H); 6.23 (broad t, 1H, N"H); 3.65 (m, 1H, H-α); 3.21 (m, 4H, H-1α/H-1β); 2.61 (dd, 1H, H-β); 2.55 (dd, 1H, H-β'); 1.48 (m, 4H, H-2α/H-2β); 1.24-1.32 (m, 44H, H-3α to H-11α/H-3β to H-15β); 0.88 (t, 6H, H-12α/H-16β)

$^{13}$C NMR ($CDCl_3$, 125.77 MHz) δ (ppm): 174.4 (CO—N'H); 171.6 (CO—N"H); 53.5 (C-α); 41.7 (C-β); 40.2, 40.0 (C-1α, C-1β); 32.6 (C-10α/C-14β); 30.2-30.4 (C-4α to C-9α, C-4β to C-13β); 30.0 (2s, C-2α/C-2β); 27.6 (2s, C-3α/C-3β); 23.4 (C-11α/C-15β); 14.8 (C-12α/C-16β)

6.2. Preparation of Compound 33

The coupling of compounds 5 and 32 is carried out by following the same experimental protocol as that described for the preparation of compound 23 in example 1 above, but using:

191.6 mg (0.16 mmol; 1 eq.) of compound 5
96 μl (0.62 mmol; 4 eq.) of DIC
86.0 mg (0.64 mmol; 4 eq.) of HOBT
122.9 mg (0.23 mmol; 1.5 eq.) of compound 32.

178 mg (0.10 mmol) of compound 33 are thus obtained.

Empirical formula: $C_{78}H_{138}N_4O_{38}$, M=1739.96 g·mol$^{-1}$

Yield: 66%

M.p.: 160° C. (decomp.)

TLC: $R_f$=0.2 eluent: $CHCl_3$/MeOH/$H_2O$ 6/3/0.5 (v/v/v)

[α]$_D^{20}$+80° (c 0.26, DMF)

IR: 3000-3500 cm$^{-1}$ (broad) ν(OH); 1652 cm$^{-1}$ ν(C=O amides)

ES-HRMS (high resolution with detection in the positive mode): m/z measured at [M+H]$^+$, calculated at 1739.9067 for $C_{78}H_{139}N_4O_{38}$ $^1$H NMR (pyridine-d$_5$, 500.13 MHz) δ (ppm): 9.17 (d, 1H, N$_\square$H); 8.82 (t, 1H, NH$_{CD}$); 8.56 (t, 1H, N"H); 8.37 (t, 1H, N'H); 4.94 (m, 1H, H-α); 5.56-5.60 (m), 5.55 (d), 5.46 (d) (6H, H-1$^{II-VII}{}_{CD}$); 5.43 (d, 1H, H-1$^I{}_{CD}$); 4.62-4.76 (m, H-3$^{II-VII}{}_{CD}$); 4.62 (H-3$^I{}_{CD}$); 4.56-4.64 (m, H-6$^{II-VII}{}_{CD}$); 4.28-4.53 (m, H-5$^{II-VII}{}_{CD}$/H-6$^{II-VII}{}_{CD}$); 4.41 (H-5$^I{}_{CD}$); 4.14-4.27 (m, H-4$^{II-VII}{}_{CD}$); 4.19 (H-6$^I{}_{CD}$); 4.06 (H-6$^{I'}{}_{CD}$); 3.98-4.13 (m, H-2$^{II-VII}{}_{CD}$); 3.92 (dd, 1H, H-2$^I{}_{CD}$); 3.80 (t, 1H, H-4$^I{}_{CD}$); 3.35, 3.30 (m, 4H, H-1α, H-1γ); 2.6-3.0 (m, H-b/H-c); 2.61 (m, H-γ/H-γ'); 2.61 (m, H-β); 2.34 (m, 1H, H-β'); 1.50, 1.47 (m, 4H, H-2α, H-2γ); 1.18 (H-3α/H-3γ); 1.05-1.25 (m, H-4α to H-11α/H-4γ to H-11γ); 0.75 (t, 6H, H-12α/H-12γ)

$^{13}$C NMR (pyridine-d$_5$, 125.77 MHz) δ (ppm): 173.7 (C-a); 173.6 (C-d); 173.2 (—CO—N'H); 172.9 (—CO—N"H); 104.1-104.6 (C-1$^{I-VII}{}_{CD}$); 85.8 (C-4$^I{}_{CD}$); 83.8-84.2 (C-4$^{II-VII}{}_{CD}$); 74.1-75.4 (C-3$^{I-VII}{}_{CD}$/C-5$^{II-VII}{}_{CD}$/C-2$^{I-VII}{}_{CD}$); 72.3 (C-5$^I{}_{CD}$); 62.7 (C-6$^I{}_{CD}$); 62.0-62.3 (C-6$^{II-VII}{}_{CD}$); 41.6 (C-α); 40.3 (C-1α/C-1γ); 33.8 (C-γ); 32.6 (C-10α/C-10γ); 32.1, 32.3 (C-b, C-c); 30.5 (C-2α/C-2γ); 30.1 (C-4α/C-4γ); 30.1-30.7 (C-5α to C-9α/C-5γ to C-9γ); 30.0 (C-β); 27.8, 27.9 (C-3α, C-3γ); 23.4 (C-11α/C-11γ); 14.8 (C-12α/C-12γ)

Example 7

Preparation of N',N"-didodecyl-N$_α$-(6$^I$-amidosuccinyl-6$^I$-deoxy-2$^I$,3$^I$-di-O-methylhexakis(2$^{II-VII}$,3$^{II-VII}$,6$^{II-VII}$-tri-O-methyl)cyclomaltoheptaose)-L-glutamide The title compound, or compound 9a, of formula:

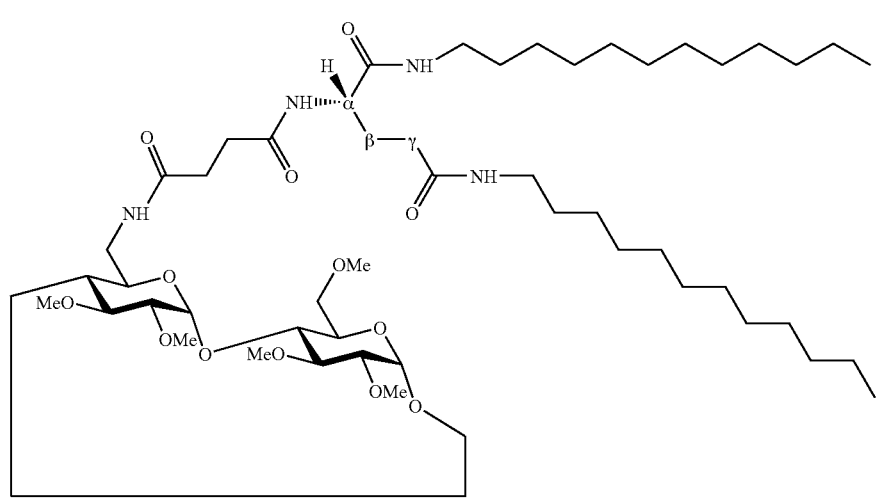

9a is obtained by coupling 6$^I$-amidosuccinyl-6$^I$-deoxy-2$^I$,3$^I$-di-O-methylhexakis(2$^{II-VII}$,3$^{II-VII}$,6$^{II-VII}$-tri-O-methyl)cyclomaltoheptaose, or Compound 13 synthesized in example 5 above, with N',N"-didodecyl-L-glutamide, or compound 22 synthesized in example 2 above, but using:

1.01 g (0.67 mmol; 1 eq.) of compound 13
415 μl (2.68 mmol; 4 eq.) of DIC
361.4 mg (2.68 mmol; 4 eq.) of HOBT
376.1 mg (0.80 mmol; 1.2 eq.) of compound 22.

605 mg (0.31 mmol, 46% yield) of compound 9a are thus obtained.

Example 8

Preparation of N',N''-dihexadecyl-N$_\alpha$-(6$^I$-amidosuccinyl-6$^I$-deoxy-2$^I$,3$^I$-di-O-methylhexakis(2$^{II-VII}$, 3$^{II-VII}$,6$^{II-VII}$-tri-O-methyl)cyclomaltoheptaose)-L-aspartamide The title compound, or compound 9b, of formula:

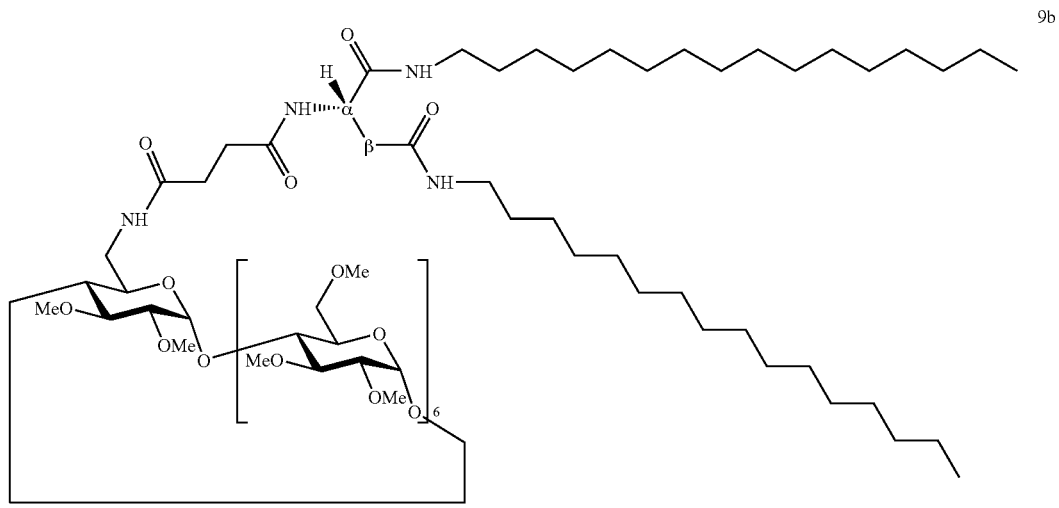

is obtained by coupling compound 13 synthesized in example 5 above with N',N''-dihexadecyl-L-aspartamide, or compound 8b.

8.1. Preparation of Compound 8b a) Preparation of N',N''-dihexadecyl-N$_\alpha$-(9-fluorenylmethoxycarbonyl)-L-aspartamide, or compound 7b, of formula

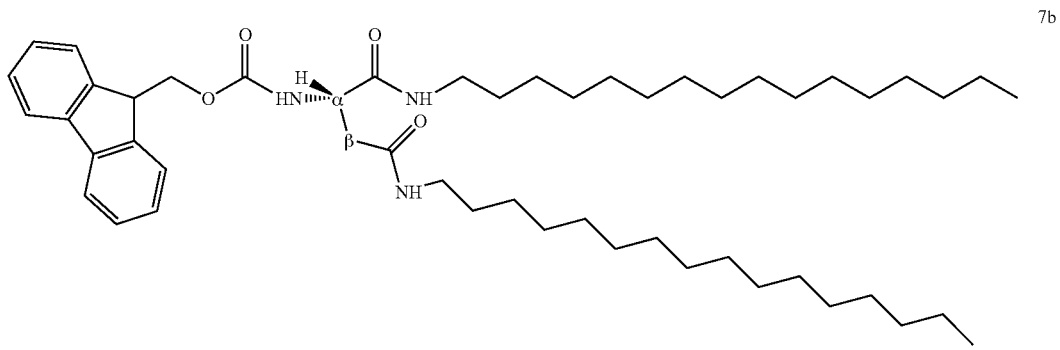

Compound 17 synthesized in example 1 above (1.5 g, 4.22 mmol, 1 eq.) is dissolved in 10 ml of DMF in a 250 ml round-bottomed flask and 2 ml (3 eq.) of DIC then 1.71 g of HOBT hydrate (3 eq.) dissolved in 8 ml of DMF are successively added. The reaction medium is maintained with stirring for 3 hours 30 min. A solution of hexadecylamine (3.06 g, 12.6 mmol, 3 eq.) in 70 ml of CHCl$_3$ is then added and then the reaction medium is left at ambient temperature for 48 hours. The mixture is concentrated under vacuum and then taken up in DMF. The precipitate is filtered off, washed with DMF and then with ether. Finally, the solid is dried under vacuum. Compound 7b is obtained with an 81% yield.

TLC: R$_f$=0.9 eluent: CHCl$_3$/MeOH 95/5 (v/v)

M.p.: 189° C.

$^1$H NMR CDCl$_3$ δ (ppm): 7.78 (d, 2H, H$_4$/H$_{4'}$, $^3$J$_{4-3}$=$^3$J$_{4'-3'}$=7.5 Hz); 7.60 (d, 2H, H$_1$/H$_{1'}$, $^3$J$_{1-2}$=$^3$J$_{1'-2'}$=7.5 Hz); 7.35 (m, 4H, H$_2$/H$_{2'}$/H$_3$/H$_{3'}$); 6.98 (broad t, 1H, N'H); 6.5 (d, 1H, N$_\alpha$H); 5.75 (broad t, 1H, N''H); 4.4-4.3 (m, H$_\alpha$/H$_8$); 4.21 (t, 1H, H$_7$, $^3$J$_{7-8}$=7.2 Hz); 3.23 (m, 4H, H$_{1\alpha}$/H$_{1\beta}$); 2.75 (d, 1H, H$_\beta$, $^3$J$_{\beta-\beta'}$=15 Hz); 2.5 (dd, 1H, H$_{\beta'}$, $^3$J$_{\beta-\beta'}$=15 Hz, $^3$J$_{\alpha-\beta'}$=7 Hz); 1.5 (m, 4H, H$_{2\alpha}$/H$_{2\beta}$); 1.4-1.1 (m, H$_{3\alpha}$ to H$_{15\alpha}$/H$_{3\beta}$ to H$_{15\beta}$); 0.9 (t, 6H, H$_{16\alpha}$/H$_{16\beta}$)

b) Preparation of Compound 8b

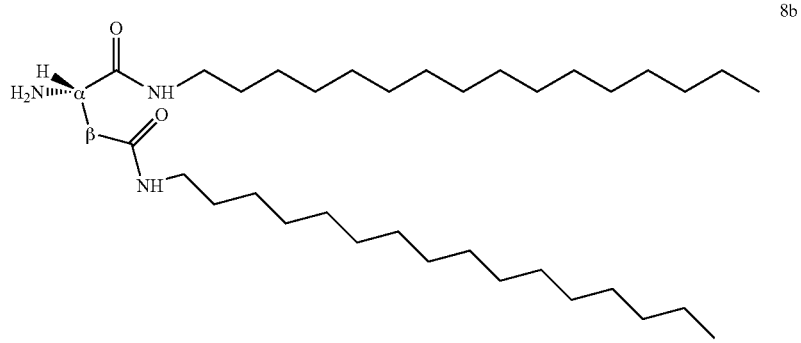

Compound 7b (1.42 g, 3.02 mmol, 1 eq.) is dissolved in 93 ml of 20% piperidine in chloroform, in a 250 ml round-bottomed flask. The reaction medium is maintained at 40° C. for 3 hours and then evaporated to dryness and finally taken up in 120 ml of chloroform. 300 ml of hexane are added and the precipitate formed is placed in a refrigerator overnight then filtered off. Washing with ethanol is carried out in order to remove the traces of piperidine. After drying in a desiccator, compound 8b is obtained with an 86% yield.

TLC: $R_f$=0.45 eluent: $CHCl_3$/MeOH 95/5 (v/v)

M.p.: 120° C.

$^1$H NMR $CDCl_3$ δ (ppm): 7.5 (broad t, 1H, N'H); 6.15 (broad t, 1H, N''H); 3.65 (t, $H_\alpha$, $^3J_{\alpha-\beta}$=$^3J_{\alpha-\beta'}$=7 Hz); 3.2 (m, 4H, $H_{1\alpha}/H_{1\beta}$); 2.6 (m, 2H, $H_\beta$, $H_{\beta'}$); 1.6-1.1 (m, $H_{2\alpha}$ to $H_{16\alpha}$/$H_{2\beta}$ to $H_{16\beta}$); 0.87 (t, 6H, $H_{16\alpha}/H_{16\beta}$)

$^{13}$C NMR $CDCl_3$ δ (ppm): 174.6 (—CO—N'H); 171.7 (—CO—N''H); 53.8 (C-α); 42.03 (C-β); 40.4-40.2 (C-1α, C-1β); 32.7 (C-14α/C-14β); 30.5-30.2 (C-2α, C-4α to C-13α/C-2β, C-4β to C-13β); 27.8 (C-3α/C-3β); 23.5 (C-15α/C-15β); 14.95 (C-16α/C-16β)

8.2. Preparation of Compound 9b

Compound 13 (500 mg, 0.33 mmol, 1 eq.) is dissolved in 15 ml of DMF in a 100 ml round-bottomed flask, and 90 µl (2 eq.) of DIC and then 50 mg (2 eq.) of HOBT dissolved in 4 ml of chloroform are successively added. After 2 hours 30 min at ambient temperature, half an equivalent of each of the reactants is again added so that all of compound 13 is used up. After 1 hour, compound 8b (287 mg, 0.5 mmol, 1.2 eq.), dissolved in 40 ml of chloroform, is added. After 24 hours at ambient temperature, the reaction is stopped with 100 µl of water and the reaction medium is concentrated to dryness in a rotary evaporator. The crude product obtained is passed over a chromatographic column on Fluka silica gel 60 (eluent gradient: $CHCl_3$/MeOH: 99/1, 97/3 and 95/5). After evaporation of all the pure fractions, compound 9b is obtained with a 30% yield.

Example 9

Preparation of N'-dodecyl-$N_\alpha$-($6^I$-amidosuccinyl-$6^I$-deoxy-$2^I,3^I$-di-O-methylhexakis($2^{II-VII},3^{II-VII},6^{II-VII}$-tri-O-methyl)cyclomaltoheptaose)-L-leucinamide The title compound, or compound 9c, of formula:

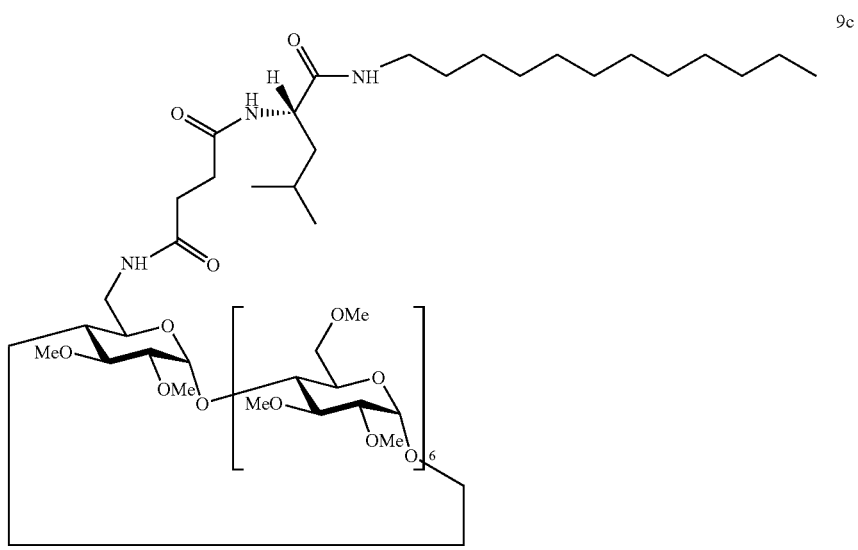

is obtained by coupling compound 13 synthesized in example 5 above with N'-dodecyl-L-leucinamide, or compound 21a.

9.1. Preparation of Compound 21a a) Preparation of N$_\alpha$-(9-fluorenylmethoxycarbonyl)-L-leucine, or compound 17a, of formula

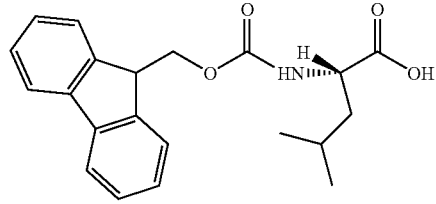

17a

Compound 17a is prepared by following the same experimental protocol as that described for the preparation of 17 in example 1, but using:
- 3.64 g (35 mmol, 1 eq.) of L-leucine
- 83 ml (105 mmol, 3.6 eq.) of a 13% (m/v) aqueous sodium carbonate solution, and
- 9.84 g (29.16 mmol, 1 eq) of N-Fmoc.

8.9 g (27.30 mmol, 93% yield) of compound 17a are thus obtained.

b) Preparation of N'-dodecyl-N$_\alpha$-(9-fluorenyl-methoxycarbonyl)-L-leucinamide, or compound 19a, of formula

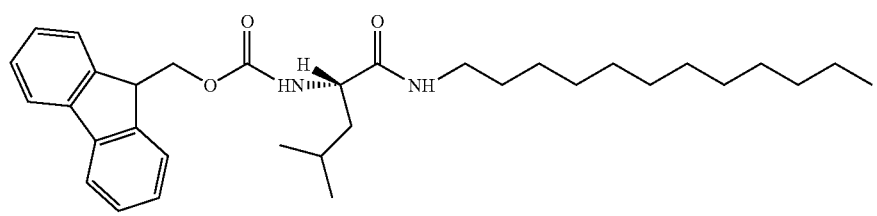

19a

Compound 19a is prepared by following the same experimental protocol as that described for the preparation of compound 19 in example 1, but using:
- 6.84 g (21 mmol, 1 eq.) of compound 17a
- 9.8 ml (63 mmol, 3 eq.) of DIC
- 8.5 g (63 mmol, 3 eq.) of HOBT
- 11.67 (63 mmol, 3 eq.) of dodecylamine.

7.25 g (14.70 mmol, 70% yield) of compound 19a are obtained.

c) Preparation of N'-dodecyl-L-leucinamide, or compound 21a, of formula

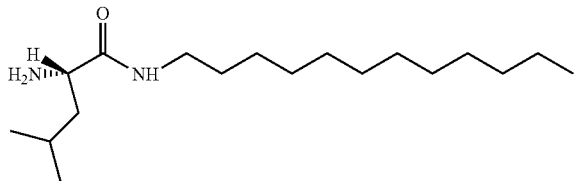

21a

Compound 21a is prepared by following the same experimental protocol as that described for the preparation of 21 in example 1 above, but using 8.2 g (16.6 mmol, 1 eq.) of compound 19a.

3.6 g (13.3 mmol, 80% yield) of compound 21a are thus obtained.

9.2. Preparation of Compound 9c

Compound 13 (427 mg, 0.28 mmol, 1 eq.) is dissolved in 15 ml of DMF in a 50 ml round-bottomed flask, and 108 μl (2.5 eq.) of DIC and then 70 mg (2.5 eq.) of HOBT dissolved in 1 ml of DMF are successively added. After 2 hours at ambient temperature, 0.25 equivalent of each of the reactants is again added so that compound 13 is used up. After 1 hour, compound 21a (100 mg, 0.33 mmol, 1.2 eq.), dissolved in 7 ml of chloroform, is added. After 18 hours at ambient temperature, the reaction is stopped with 100 μL of water and the reaction medium is concentrated to dryness in a rotary evaporator. The crude product obtained is passed over a chromatography column of Fluka silica gel 60 (elution gradient: CHCl$_3$/MeOH: 99/1 (v/v) then 97/3 (v/v)).

Example 10

Preparation of N',N''-dodecyl-N$_\alpha$-(6$^I$-amidosuccinyl-6$^I$-deoxy-per(2,3,6-di-O-methyl)cyclomaltoheptaose)-β-alanine The title compound, or compound 9d, of formula:

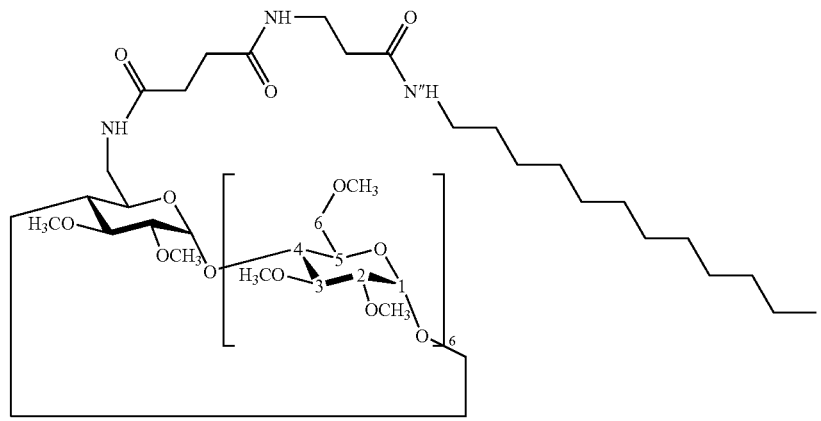

9d is obtained by coupling 6$^I$-amidosuccinyl-6$^I$-deoxy-per(2,3,6-tri-O-methyl)cyclomaltoheptaose, or compound 5a, with N-dodecyl-N$_\alpha$-(9-fluorenylmethoxycarbonyl)-β-alanine, or Compound 7c.

10.1. Preparation of Compound 5a a) Preparation of 6$^I$-azido-6$^I$-deoxy-per(2,3,6-tri-O-methyl)cyclomaltoheptaose, or compound 3a, of formula

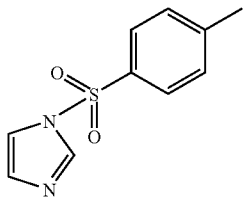

3a

Sodium hydride (coated at 60% m/m) (11.01 g, 0.46 mol, 88 eq.) is suspended in 150 ml of anhydrous DMF and under an inert atmosphere in a clean and dry two-necked flask. A solution obtained by dissolving compound 3 (3.64 g, 0.0031 mol, 1 eq.) synthesized in example 1 in 240 ml of anhydrous DMF, is added under an inert atmosphere and at ambient temperature. After 1 hour 30 min, the reaction medium is cooled to 0° C. and methyl iodide (38 ml, 0.6 mol, 190 eq.) is added dropwise. The reaction medium is left at ambient temperature for 72 hours and the reaction is then stopped with 6 ml of water. The precipitate formed is filtered off and washed with DMF. The filtrate is concentrated in a rotary evaporator. The pasty residue is taken up in water and extracted with chloroform (5×50 ml). The organic phase is washed with water (3×100 ml). The organic phases are combined, dried over Na$_2$SO$_4$, filtered then evaporated. The residue is taken up a final time in water and the suspension is left to separate by settling out overnight in order to remove the fats containing the sodium hydride. After evaporation and lyophilization, compound 3a is obtained with a quantitative yield.

TLC: R$_f$=0.9 eluent: CHCl$_3$/MeOH 9/1 (v/v)

M.p.: 80° C. (decomposition)

$^1$H NMR CDCl$_3$ δ (ppm): 5.2-5 (m, 7H, H$_1$-CD); 4-3.25 (m, H$_3$-CD/H$_4$-CD/H$_5$-CD/H$_6$-CD/H$_6$'-CD/OCH$_3$-CD); 3.25-3.1 (dd, 7H, H$_2$-CD, $^3$J$_{1-2}$=10 Hz/$^3$J$_{2-3}$=4 Hz)

b) Preparation of 6$^I$-amino-6$^I$-deoxy-per(2,3,6-tri-O-methyl)cyclomaltoheptaose, or compound 4a, of formula

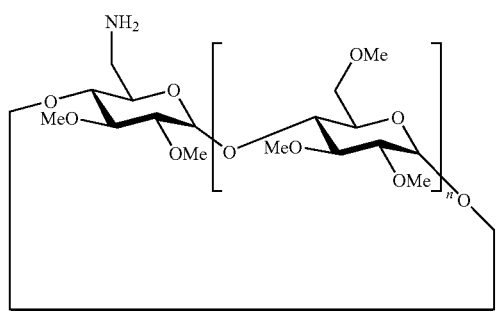

4a

Compound 3a (4.33 g, 3 mmol, 1 eq.) is dissolved in 220 ml of DMF, in a 1 litre round-bottomed flask. A solution of triphenylphosphine (3.15 g, 0.012 mol, 4 eq.) dissolved in 13 ml of DMF is added slowly. After stirring for 3 hours at ambient temperature, the reaction medium is cooled to 0° C. and 115 ml of 20% aqueous ammonia are added. The mixture is stirred overnight at ambient temperature and then concentrated in a rotary evaporator. The oily residue is taken up in 250 ml of water and the white precipitate formed is filtered off and washed with 2×40 ml of water. The filtrate is then concentrated under vacuum, the solid residue is taken up in a minimum of water and then brought to a pH of 4.5 (initial pH=8.2), the insoluble material is filtered off and the filtrate is passed over a column of Lewatit® SP 1080 resin. Compound 4a is detached with 6% aqueous ammonia and the filtrate is then concentrated in a rotary evaporator, taken up in a minimum of water then lyophilized. Compound 4a is obtained with an overall yield of 60%.

TLC: R$_f$=0.25 eluent: CHCl$_3$/MeOH 95/5 (v/v)

M.p.: 80° C. (decomposition)

$^1$H NMR (CDCl$_3$, 500.13 MHz) δ (ppm): 5.36 (d, 1H, H-1$^I_{CD}$, $^3$J$^I_{1-2}$=3.6 Hz); 5.30-5.35 (m, 6H, H-1$^{II-VII}_{CD}$); 3.86-3.96 (m, H-5$^{II-VII}_{CD}$); 3.87-3.92 (m, H-6$^{II-VII}_{CD}$); 3.83 (H-5$^I_{CD}$); 3.75-3.83 (m, H-4$^{II-VII}_{CD}$); 3.76 (H-3$^I_{CD}$); 3.69-3.79 (m, H-3$^{II-VII}_{CD}$); 3.71 (H-4$^I_{CD}$); 3.65-3.73 (m, H-6$^{II-VII}_{CD}$); 3.64-3.66 (m, OCH$_3$-6$_{CD}$); 3.55-3.57 (m, OCH$_3$-3$_{CD}$); 3.43 (H-2$^I_{CD}$); 3.42-3.43 (m, OCH$_3$-2$_{CD}$); 3.36-3.44 (m, H-2$^{II-VII}_{CD}$); 3.05 (dd, 1H, H-6$^I_{CD}$, $^3$J$^I_{6-5}$=5.5 Hz, $^3$J$^I_{6-6'}$=14.2 Hz); 2.96 (dd, 1H, H-6$^{'I}_{CD}$, $^3$J$^I_{6'-5}$=3.0 Hz, $^3$J$^I_{6'-6}$=14.2 Hz)

c) Preparation of 6$^I$-amidosuccinyl-6$^I$-deoxy-per(2,3,6-tri-O-methyl)cyclomaltoheptaose, or Compound 5a, of formula

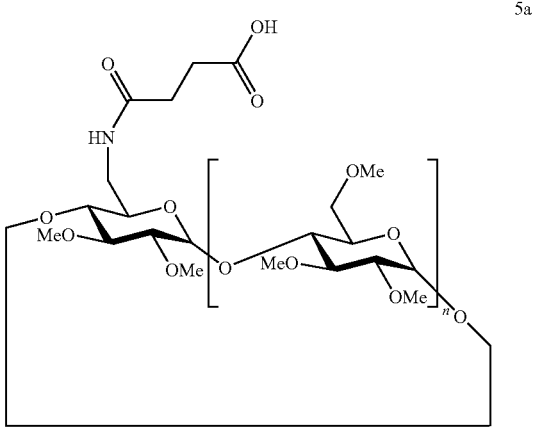

5a

Compound 4a (1.5 g, 1.08 mmol, 1 eq.) is dissolved in 30 ml of anhydrous DMF, under an inert atmosphere, in a clean and dry 100 ml round-bottomed flask. Succinic anhydride (0.170 g, 1.7 mmol, 1.6 eq.) dissolved in 8 ml of anhydrous DMF is added. The reaction medium is left under an inert atmosphere for 20 hours at ambient temperature. The reaction is stopped with 170 μl of water and the insoluble material is then filtered off over paper. The filtrate is concentrated in a rotary evaporator and then the residue is taken up in a minimum of water and lyophilized. Compound 5a is obtained with a 76% yield.

TLC: R$_f$=0.5 eluent: CHCl$_3$/MeOH 9/1 (v/v)

M.p.: 80° C. (decomposition)

$^1$H NMR CDCl$_3$ δ (ppm): 6.4 (t, 1H, NH-CD, $^3$J$_{NH-H6}$=6 Hz); 5.25-5 (m, 7H, H$_1$-CD); 3.95-3.25 (m, H$_3$-CD/H$_4$-CD/H$_5$-CD/H$_6$-CD/H$_6$'-CD/OCH$_3$-CD); 3.25-3.15 (m, H$_2$-CD); 2.75-2.4 (m, 4H, H$_b$/H$_c$)

10.2. Preparation of N-dodecyl-$N_\alpha$-(9-fluorenyl-methoxycarbonyl)-β-alanine, or compound 7c, of formula

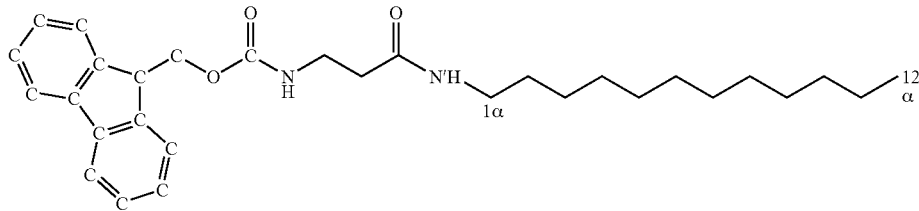

7c $N_\alpha$-(9-fluorenylmethoxycarbonyl)-L-β-alanine (commercial product) (2 g, 6.42 mmol, 1 eq.) is dissolved in 12 ml of DMF, in a 100 ml round-bottomed flask and 3 ml (3 eq.) of DIC and then 1.93 g of HOBT hydrate (3 eq.) dissolved in 7 ml of DMF are successively added. The reaction medium is maintained with stirring for 2 hours. A solution of dodecylamine (1.75 g, 9.46 mmol, 1.5 eq.) in 40 ml of chloroform is then added and the reaction medium is then left at ambient temperature for 18 hours. The mixture is concentrated under vacuum and then taken up in DMF. After 3 hours in a refrigerator, the precipitate is filtered off, washed with DMF and then dried with ether. The filtrate is recovered and reprecipitated in the refrigerator. The precipitate obtained is filtered off and dried with ether. Finally, the solid is dried under vacuum. Compound 7c is obtained with a 47% yield.

TLC: $R_f$=0.8 eluent: $CHCl_3$/MeOH 95/5 (v/v)

M.p.: 143° C.

$^1$H NMR ($CDCl_3$, 500.13 MHz) δ (ppm): 7.78 (d, 2H, $H_4/H_{4'}$, $^3J_{4-3}=^3J_{4'-3'}$=7.5 Hz); 7.60 (d, 2H, $H_1/H_{1'}$, $^3J_{1-2}=^3J_{1'-2'}$=7.5 Hz); 7.35 (m, 4H, $H_2/H_{2'}/H_3/H_{3'}$); 5.55 (broad t, 1H, NH); 5.52 (broad t, 1H, NH); 4.36 (d, 2H, $H_8$, $^3J_{7-8}$=2.8 Hz); 4.21 (t, 1H, $H_7$, $^3J_{7-8}$=2.8 Hz); 3.5 (m, 2H, $H_\alpha$); 3.23 (q, 2H, $H_{1\alpha}$); 2.4 (t, 2H, $H_\beta$, $^3J_{\alpha-\beta}$=2.2 Hz) 1.6 (m, 2H, $H_{2\alpha}$); 1.4-1.1 (m, $H_{3\alpha}$ to $H_{11\alpha}$); 0.89 (t, 3H, $H_{12\alpha}$)

10.3. Preparation of Compound 9d

Compound 5a (780 mg, 0.51 mmol, 1 eq) is dissolved in 30 ml of DMF in a 100 ml round-bottomed flask and 220 µl (2.75 eq.) of DIC and then 142 mg (2.75 eq.) of HOBT dissolved in 2 ml of DMF are successively added. After 3 hours 30 min, compound 7c (160 mg, 0.62 mmol, 1.2 eq.) dissolved in 6 ml of chloroform is added. After 24 hours at ambient temperature, the reaction is stopped with 100 µl of water and the reaction medium is concentrated to dryness in a rotary evaporator. The crude product obtained is passed over a chromatography column on silica gel (eluent gradient: $CHCl_3$/MeOH).

In the above examples, the thin layer chromatographies (TLC) were carried out on aluminium plates (5×7.5 cm) coated with silica gel 60 $F_{254}$ (Merck). The compounds were revealed under UV light (λ=254 nm), by spraying of a 10% aqueous $H_2SO_4$ solution followed by a heating step for all the cyclodextrin derivatives, or by spraying of a 0.2% solution of ninhydrin in ethanol followed by a heating step for the compounds having a primary amine function.

The melting points were determined using a Köfler bench requiring calibration with reference products from Merck Eurolab.

The proton and carbon NMR experiments were recorded routinely, respectively, at the frequency of 200.13 MHz and 50.32 MHz on a Brucker AC 200 device equipped with a multinuclear probe ($^1$H, $^{13}$C, $^{15}$N, $^{31}$P). The chemical shifts are given with respect to an external reference, tetramethylsilane (δ=0 ppm), and the internal calibrations were carried out using a residual solvent signal, with a possible correction for the water signal as a function of the temperature. The deuterated solvents used ($D_2O$, DMSO-$d_6$, $CDCl_3$, Pyr-$d_5$) came from Eurisotop. The measurements were carried out using rigorous control of the temperature (+/−0.1 K) at 298 K, unless specified. The 90° pulse values were around 10 µs for $^1$H (attenuation 0 dB), and around 20 µs for $^{13}$C (attenuation 2 dB).

The one-dimensional spectra were acquired over 16 K points, and transformed over 32 K points (zero-filling). A possible baseline correction was carried out on the spectra.

In order to facilitate the signal assignment, one and two-dimensional spectra were effected. They were recorded, respectively, at the frequency of 500.13 MHz and 125.77 MHz on a Brucker DRX 500 device equipped with a Broad Band Inverse (bbi) with 3 axes at 5 mm and acquired over 2048 points in F2 with 256 time increments in F1, the recycling time for each scan being approximately 1.5 seconds. The phase experiments were acquired in TPPI mode, and transformed into a matrix of 1K×1K points (real-real matrix). The spectra were processed with a π/2 shifted sinus apodization function in both dimensions, with a baseline correction.

All the spectra were processed using Mestrec or UXNMR software (Brucker Analytische Messtechnik) on the INDY workstation (Silicon Graphics) or on a PC.

In order to facilitate the analysis of the spectra, the following abbreviations were adopted: s, singlet; d, doublet; dd, resolved doublet; t, triplet; tl, broad triplet; q, quadruplet, and m, multiplet.

BIBLIOGRAPHY

[1] FR-A-2 792 942.
[2] Auzély-Velty et al., *Carbohydrate Research*, 1999, 318, 82-90.

The invention claimed is:
1. Cyclodextrin derivative corresponding to formula (I):

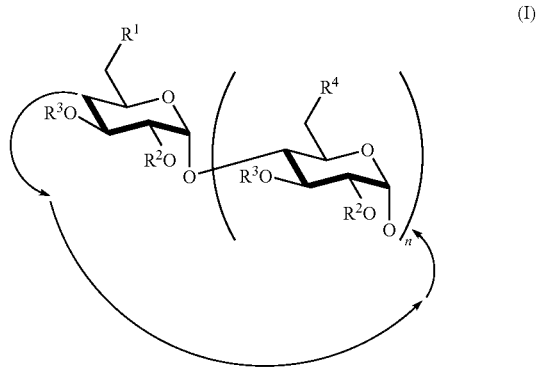

(I)

in which:

$R^1$ corresponds to formula (II):

—NH-E-AA-$(L^1)_p(L^2)_q$ (II)

in which:

E represents a linear or branched, saturated or unsaturated hydrocarbon-based group comprising from 1 to 15 carbon atoms and optionally comprising one or more hetero atoms;

AA represents the residue of an amino acid;

$L^1$ and $L^2$, which may be identical or different, correspond to formula (IV): -$G^2$-Y, in which $G^2$ represents a —CO—, —NH— or —NR— group where R is an $C_1$ to $C_6$ alkyl group, while Y represents a $C_8$ to $C_{18}$ linear alkyl chain;

p and q, which may be identical or different, are integers equal to 0 or to 1, on the condition however that at least one of these integers is other than 0;

$R^2$ represents a hydrogen atom, a methyl group, an isopropyl group, a hydroxypropyl group or a sulphobutyl ether group;

$R^3$ represents a hydrogen atom or is identical to $R^2$, except when $R^2$ is a hydroxypropyl group;

all the $R^4$ represent either a hydroxyl group, or $R^2$, except when $R^2$ is a hydroxypropyl group, or else one or more $R^4$ are identical to $R^1$ and the other $R^4$ represent(s) either a hydroxyl group, or $R^2$, except when $R^2$ is a hydroxypropyl group;

n is an integer equal to 5, 6 or 7.

2. Derivative according to claim 1, in which, in formula (II), E corresponds to formula (III): —CO—X-$G^1$-, in which X represents a bridge-forming alkylene group comprising 1 to 8 carbon atoms, while $G^1$ represents a —CO—, —NH— or —NR— group in which R is a $C_1$ to $C_6$ alkyl group.

3. Derivative according to claim 2, in which, in formula (III), X represents a bridge-forming alkylene group comprising from 1 to 4 carbon atoms.

4. Derivative according to claim 1, in which, in formula (II), AA represents the residue of an amino acid chosen from aspartic acid, glutamic acid, alanine, arginine, asparagine, cysteine, glutamine, glycine, histidine, isoleucine, leucine, lysine, methionine, phenylalanine, proline, serine, threonine, tyrosine, tryptophan and valine.

5. Derivative according to claim 4, in which, in formula (II), AA represents the residue of an amino acid chosen from aspartic acid, glutamic acid, isoleucine, leucine and phenylalanine.

6. Derivative according to claim 1, in which, in formula (II), AA represents the residue of an amino acid belonging to the L series.

7. Derivative according to claim 1, in which, in formula (IV), Y represents a $C_{12}$ to $C_{16}$ alkyl chain.

8. Derivative according to claim 1, in which, in formula (II), E is bonded via an amide bond to the residue AA, this residue being itself bonded via an amide bond to the group(s) $L^1$ and/or $L^2$.

9. Derivative according to claim 1, in which, in formula (II), E corresponds to the formula: —CO—X—CO— in which X represents a bridge-forming alkylene group comprising 1 to 4 carton atoms, while $L^1$ and $L^2$ correspond to the formula: —NH—Y in which Y represents a $C_8$ to $C_{18}$ linear alkyl chain.

10. Derivative according to claim 1, in which, in formula (I), $R^1$ corresponds to the specific formula (VI):

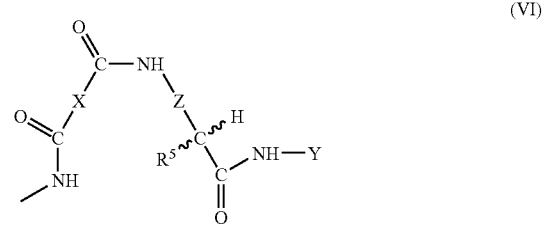

in which:

X represents a bridge-forming alkylene group comprising 1 to 4 carton atoms and Y represents a $C_8$ to $C_{18}$ linear alkyl chain;

while

Z represents:

either a covalent bond, in which case $R^5$ represents a hydrogen atom, a methyl group, the side chain of an amino acid or a group of formula: —$(CH_2)_t$—CO—NH—Y in which t is 1 or 2 and Y represents a $C_8$ to $C_{18}$ linear alkyl chain, or a bridge-forming hydrocarbon-based group, comprising from 1 to 4 carbon atoms and comprising one or more hetero atoms chosen from O and N, in which case $R^5$ represents a primary amine group or a group of formula: —NH—CO—Y in which Y represents a $C_8$ to $C_{18}$ linear alkyl chain.

11. Derivative according to claim 10, in which, in formula (VI):

Z represents a covalent bond;

Y represents a $C_8$ to $C_{18}$ linear alkyl chain;

while $R^5$ represents a branched alkyl group containing 4 carbon atoms, a benzyl group or a group of formula: —$(CH_2)_t$—CO—NH—Y, in which t is equal to 1 or 2 and Y represents a $C_8$ to $C_{18}$ linear alkyl chain.

12. Derivative according to claim 10, in which, in formula (VI):

Z represents a covalent bond;

Y represents a $C_8$ to $C_{18}$ linear alkyl chain;

while $R^5$ represents a group of formula: —$(CH_2)_t$—CO—NH—Y, in which t is equal to 1 or 2 and Y represents a $C_8$ to $C_{18}$ linear alkyl chain.

13. Derivative according to claim 1, which comprises only one substituent $R^1$ per molecule of derivative.

14. Derivative according to claim 1, in which, in formula (I), n is equal to 6.

15. Derivative according to claim 1, which is chosen from:

N',N''-didodecyl-$N_\alpha$-($6^I$-amidosuccinyl-$6^I$-deoxycyclomaltoheptaose)-L-aspartamide, N',N''-didodecyl-$N_\alpha$-($6^I$-amidosuccinyl-$6^I$-deoxycyclomaltoheptaose)-L-glutamide, N',N''-didodecyl-$N_\alpha$-($6^I$-amidosuccinyl-$6^I$-deoxy-$2^I$-O-methylhexakis($2^{II-VII}$,$6^{II-VII}$di-O-methyl)cyclomaltoheptaose)-L-aspartamide, N',N''-didodecyl-$N_\alpha$-($6^I$-amidosuccinyl-$6^I$-deoxy-$2^I$-O-methylhexakis($2^{II-VII}$,$6^{II-VII}$-di-O-methyl)cyclomaltoheptaose)-L-glutamide, N',N''-didodecyl-$N_\alpha$-($6^I$-amidosuccinyl-$6^I$-deoxy-$2^I$,$3^I$-di-O-methylhexakis($2^{II-VII}$,$3^{II-VII}$$6^{II-VII}$-tri-O-methyl)cyclomaltoheptaose)-L-aspartamide, N'-dodecyl-N''-hexadecyl-$N_\alpha$-($6^I$-amidosuccinyl-$6^I$-deoxycyclomaltoheptaose)-L-aspartamide, N',N''-didodecyl-$N_\alpha$-($6^I$-amidosuccinyl-$6^I$-deoxy-$2^I,3^I$-di-O-methylhexakis($2^{II-VII},3^{II-VII},6^{II-VII}$-tri-O-methyl)cyclomaltoheptaose)-L-glutamide, N',N''-dihexadecyl-$N_\alpha$-($6^I$-amidosuccinyl-$6^I$-deoxy-$2^I,3^I$-di-O-methylhexakis($2^{II-VII},3^{II-VII},6^{II-VII}$-tri-O-methyl)cyclomaltoheptaose)-L-aspartamide, and N'-dodecyl-$N_\alpha$-($6^I$-amidosuccinyl-$6^I$-deoxy-$2^I,3^I$-di-O-methylhexakis($2^{II-VII},3^{II-VII},6^{II-VII}$-tri-O-methyl)cyclomaltoheptaose)-L-leucinamide.

16. Process for preparing a cyclodextrin derivative according to claim 1, which comprises a step in which a cyclodextrin derivative of formula (VII):

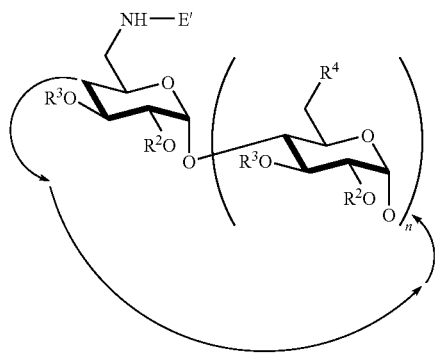

(VII)

in which:

E' represents a linear or branched, saturated or unsaturated hydrocarbon-based group, comprising from 1 to 15 carbon atoms, one or more hetero atoms and a free functional group capable of reacting with a hydroxyl, amine, carboxylic acid or thiol group of an amino acid so as to form a covalent bond;

$R^2$ represents a hydrogen atom, a methyl group, an isopropyl group, a hydroxypropyl group or a sulphobutyl ether group;

$R^3$ represents a hydrogen atom or is identical to $R^2$, except when $R^2$ is a hydroxypropyl group;

all the $R^4$ represent either a hydroxyl group, or $R^2$, except when $R^2$ is a hydroxypropyl group, or else one or more $R^4$ represent an —NH-E' group and the other $R^4$ represent(s) either a hydroxyl group, or $R^2$, except when $R^2$ is a hydroxypropyl group;

n is an integer equal to 5, 6 or 7;

is reacted with a compound of formula (VIII):

(VIII)

in which:

AA' represents an amino acid comprising a free hydroxyl, amine, carboxylic acid or thiol group;

$L^1$ and $L^2$, which may be identical or different, correspond to formula (IV): -$G^2$-Y, in which $G^2$ represents a —CO—, —NH— or —NR— group where R is an $C_1$ to $C_6$ alkyl group, while Y represents a $C_8$ to $C_{18}$ linear alkyl chain;

p and q, which may be identical or different, are integers equal to 0 or to 1, on the condition however that at least one of these integers is other than 0.

17. Process according to claim 16, which also comprises a step consisting in reacting a monoamine cyclodextrin derivative of formula (IX):

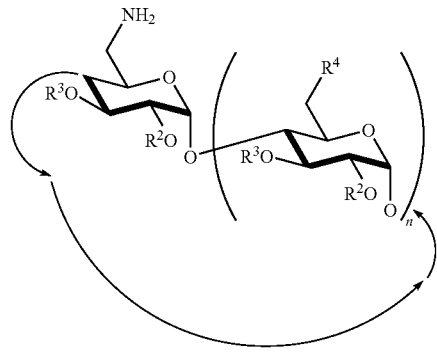

(IX)

in which:

$R^2$, $R^3$ and n have the same meaning as in formula (VII);

all the $R^4$ represent either a hydroxyl group, or $R^2$, except when $R^2$ is a hydroxypropyl group, or else one or more $R^4$ represent(s) an —$NH_2$ group and the other $R^4$ represent(s) either a hydroxyl group, or $R^2$, except when $R^2$ is a hydroxypropyl group, with a compound that is a precursor of the group E' comprising a free functional group capable of reacting with the amine group of the derivative of formula (IX), so as to obtain the cyclodextrin derivative of formula (VII).

18. Process according to claim 16, which also comprises the steps consisting in:

reacting an amino acid, in which the functional group intended to react with the free functional group of the group E' of the cyclodextrin derivative of formula (VII) has been protected beforehand, with a compound that is a precursor of the group $L^1$ and/or a compound that is a precursor of the group $L^2$, this or these precursor compound(s) comprising a free functional group capable of reacting with a hydroxyl, amine, carboxylic acid or thiol group of an amino acid so as to form a covalent bond; then deprotecting the protected functional group of the amino acid, so as to obtain the compound of formula (VIII).

19. Process according to claim 17, in which the compound that is a precursor of the group E' is an acid anhydride of formula (X):

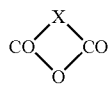

(X)

in which X represents a bridge-forming alkylene group comprising 1 to 4 carton atoms, which is reacted with the monoamine cyclodextrin derivative of formula (IX) in an anhydrous medium and under an inert atmosphere.

20. Process according to claim 16, in which the cyclodextrin derivative of formula (VII) and the compound of formula (VIII) are reacted in the presence of N,N'-diisopropylcarbodiimide (DIC) and hydroxybenzotriazole (HOBT).

21. Inclusion complex of a cyclodextrin derivative according to claim 1, and a hydrophobic compound.

22. Inclusion complex according to claim 21, in which the hydrophobic compound is a medicinal active ingredient.

23. Inclusion complex according to claim 21, in which the hydrophobic compound is a cell membrane detergent.

24. Organized surfactant system comprising a cyclodextrin derivative according to claim 1 or an inclusion complex according to claim 21.

25. Organized surfactant system according to claim 24, in which the surfactant is a phospholipid.

26. Derivative according to claim 10, in which, in formula (VI):

Z represents a covalent bond;

Y represents a $C_{12}$ to $C_{16}$ linear alkyl chain;

while $R^5$ represents a branched alkyl group containing 4 carbon atoms, a benzyl group or a group of formula: —$(CH_2)_t$—CO—NH—Y, in which t is equal to 1 or 2 and Y represents a $C_{12}$ to $C_{16}$ linear alkyl chain.

27. Derivative according to claim 10, in which, in formula (VI):

Z represents a covalent bond;

Y represents a $C_{12}$ to $C_{16}$ linear alkyl chain;

while $R^5$ represents a group of formula: —$(CH_2)_t$—CO—NH—Y, in which t is equal to 1 or 2 and Y represents a $C_{12}$ to $C_{16}$ linear alkyl chain.

* * * * *